(12) United States Patent
Kwak et al.

(10) Patent No.: US 7,897,835 B2
(45) Date of Patent: Mar. 1, 2011

(54) EXPRESSION VECTORS PSSA-K AND PSSA-H FOR EXPRESSION OF SOD AND APX IN PLANTS TO PROVIDE STRESS TOLERANCE

(75) Inventors: Sang-Soo Kwak, Taejeon-si (KR); Suk-Yoon Kwon, Taejeon-si (KR); Haeng-Soon Lee, Taejeon-si (KR); Li Tang, Taejeon-si (KR); Soon Lim, Taejeon-si (KR); Byung-Hyun Lee, Kyeongsangnam-do (KR)

(73) Assignee: Korea Research Institute of Bioscience and Biotechnology, Taejeon-Si (KR)

( * ) Notice: Subject to any disclaimer, the term of this patent is extended or adjusted under 35 U.S.C. 154(b) by 967 days.

(21) Appl. No.: 11/718,661

(22) PCT Filed: Jan. 28, 2005

(86) PCT No.: PCT/KR2005/000258
§ 371 (c)(1),
(2), (4) Date: May 7, 2007

(87) PCT Pub. No.: WO2006/054815
PCT Pub. Date: May 26, 2006

(65) Prior Publication Data
US 2008/0244792 A1    Oct. 2, 2008

(30) Foreign Application Priority Data
Nov. 17, 2004  (KR) .................. 10-2004-0093945

(51) Int. Cl.
*C12N 15/82* (2006.01)
*A01H 5/00* (2006.01)
*C07H 21/04* (2006.01)

(52) U.S. Cl. .............. 800/278; 800/293; 800/294; 800/295; 800/298; 536/23.2; 435/320.1

(58) Field of Classification Search .............. None
See application file for complete search history.

(56) References Cited

U.S. PATENT DOCUMENTS
5,538,878 A    7/1996   Thomas et al.

OTHER PUBLICATIONS

Kwon et al. Enhanced tolerances of transgenic tobacco plants expressing both superoxide dismutase and ascorbate peroxidase in chloroplasts against methyle viologen-mediated oxidative stress. (2002) Plant, Cell and Environment; vol. 25; pp. 873-882.*
Kim et al. A novel oxidative stress-inducible peroxidase promoter from sweet potato: molecular cloning and characterization in transgenic tobacco plants and cultured cells. (2003) Plant Molecular Biology; vol. 51; pp. 831-838.*
Tang et al. Selection of transgenic potato plants expressing both CuZnSOD and APX in chloroplasts with enhanced tolerance to oxidative stress. (2004) Korean J. Plant Biotechnol.; vol. 31; pp. 109-113.*
Romano et al. Transgene organisation in potato after particle bombardment-mediated (co-)transformation using plasmids and gene cassettes. (2003) Transgenic Research; vol. 12; pp. 461-473.*
Mario Niepel, et al., Identification and Characterization of the Functional Elements . . . , Journal of Virology, vol. 73, No. 11, pp. 9080-9088, 1999.
Yelena Kovtun, et al., PNAS, vol. 97, No. 6, pp. 2940-2945, 2000.
Randy D. Allen, et al., Dissection of Oxidative Stress Tolerance . . . , Plant. Physiol, 107, pp. 1049-1054, 1995.
Hong-Li, Lian et al., The Role of Aquaporin RWC3 . . . , Plant Cell Physiol., vol. 45, pp. 481-489, 1994.

* cited by examiner

*Primary Examiner*—Cathy Kingdon Worley
(74) *Attorney, Agent, or Firm*—Lucas & Mercanti, LLP

(57) ABSTRACT

The present invention relates to a recombinant expression vector, pSSA-K or pSSA-H, containing oxidative stress inducible promoter, such as sweetpotato peroxidase anionic 2 (SWEPA2), a nucleotide encoding superoxide dismutase (SOD) and a nucleotide sequence encoding ascorbate peroxidase (APX) linked to the promoter, antibiotics resistant gene, tobacco etch virus leader sequence, a polynucleotide enclodging a transit peptide for chloroplast targeted expression, CaMV 35S transcription terminator, and T-DNA boarder sequence, and a method for preparing multiple stress tolerant transgenic plants using the recombinant expression vector.

7 Claims, 17 Drawing Sheets

A

C

B

EXPRESSION VECTORS PSSA-K AND PSSA-H FOR EXPRESSION OF SOD AND APX IN PLANTS TO PROVIDE STRESS TOLERANCE

CROSS-REFERENCE TO RELATED APPLICATIONS

This application is a 371 of PCT/KR2005/000258 filed Jan. 28, 2005, which claims the benefit of Korean Patent Application No. 10-2004-0093945 filed Nov. 17, 2004, the contents of each of which are incorporated herein by reference.

TECHNICAL FIELD

The present invention relates to recombinant expression vectors for production of plants having multiple stress tolerance, which are prepared by attaching multiple stress tolerant genes to oxidative stress inducible promoter originated from sweetpotato to express the gene in chloroplasts, multiple stress tolerant plants transformed with the above vector, and a preparation method for the plants.

BACKGROUND ART

Most living things including plants are easily affected by not only biological stresses such as pathogen, insect, virus, etc, but also in variety of environmental stresses such as high temperature, salt, drought, pollution, wound, cold injury, excessive light condition, ozone, sulfur dioxide, over-exposure of UV, osmotic shock, etc. When plants are affected by various environmental stresses like the above, oxygen therein, which is essential for life-support, changes into reactive oxygen free radicals including superoxide anion radical ($O^{2-}$), hydrogen peroxide ($H_2O_2$), hydroxyl radical, etc, causing serious physiological disorders in vivo. Precisely, small amount of oxygen free radical in vivo is enough to transmit signal in cells and induce the expression of genes (antioxidant enzyme, heat shock protein, etc.) necessary for self-defense in a plant. However, the increase of reactive oxygen free radicals causes physiological disorders, by dose-dependent manner, even to cell death.

Recently, many researchers are deeply interested in signal transduction pathway mediated by oxygen free radicals in plants. That is because the regulation of that pathway enables the increase of the expressions of antioxidant enzyme and host-defense protein in cells and leads to the development of plants having strong resistance against any environmental stress (Kovtun, et al., Proc. Natl. Acad. Sci. USA, 97(6): 2940-2945, 2000). According to a recent report, MAP kinase cascade (MARK cascade) plays an important role in signal transduction pathway mediated by oxygen free radicals in plants (Kovtun, et al., Proc. Natl. Acad. Sci. USA, 97(6): 2940-2945, 2000).

Superoxide dismutase (SOD) is an enzyme that converts superoxide anion radical ($O^{2-}$) into hydrogen peroxide ($H_2O_2$), and is divided into CuZnSOD, MnSOD and FeSOD according to metal cofactor included in the enzyme. These are located differently in cells, for example CuZnSOD is found in cytoplasm and chloroplasts, MnSOD is found in mitochondria and FeSOD exists in chloroplasts. SOD is an important environmental tolerant factor that eliminates oxygen free radicals generated in a living body by environmental stress, which can be useful for the production of medical supplies, food, cosmetics, etc. And thus, preparing a transgenic plant containing SOD gene showing a strong environmental stress tolerance leads to the development of a plant having a strong resistance to environmental stresses such as ozone, low temperature, herbicides, etc (Plant Physiology, 10: 1049-1054, 1995; U.S. Pat. No. 5,538,878).

Ascobate peroxidase (APX) is an enzyme that converts $H_2O_2$ into water by using ascobate as an electron donor, and is largely found in plants and insects. This enzyme is known to exist in cytoplasm, stroma in chloroplasts and thylakoid membrane in plants (Free Rad. Biol. Med. 23: 473-479, 1997).

In chloroplasts of a plant, oxygen content is relatively high and electron transport system is operating to utilize electronic energy produced from the decomposition of water with light energy, so this organ is very sensitive to various oxidative stresses. Thus, the increase of anti-oxidative capability of chloroplast might be a great help to maintain productivity of a plant under environmental stresses.

As of today, in order to develop a stress tolerant plant, CaMV 35S promoter, which is constitutively expressed regardless of conditions, has been mostly used for the combination with a gene with resistance for specific stress to construct an expression vector. So, the resultant plant has resistance against only a specific stress. In order to overcome this problem, it is required to prepare an expression vector including a promoter being able to be expressed under any stress circumstances and a stress tolerant gene, and a transgenic plant transfected with the vector.

In order to develop transgenic agricultural crops having tolerance against environmental disaster, the present inventors prepared a novel expression vector for plant transformation by attaching multiple stress tolerant genes SOD (superoxide dismutase) and APX (ascorbate peroxidase) to oxidative stress inducible peroxidase promoter SWPA2 originated from sweetpotato so as to express the genes in chloroplasts of a plant. And then, the inventors regenerated transformed plants prepared from potato, sweetpotato and tall fescue by tissue culture. At last, the present inventors completed this invention by confirming that the transgenic plants of the invention have increased multiple stress tolerance.

DISCLOSURE

Technical Problem

It is an object of the present invention to provide a recombinant expression vector for plant transformation that is prepared by attaching multiple stress tolerant genes to oxidative stress inducible promoter originated from sweetpotato so as to express the genes in chloroplasts.

It is another object of the present invention to provide a multiple stress tolerant plant transformed with the above expression vector and a preparation method for the same.

Technical Solution

In order to achieve the above objects, the present invention provides recombinant expression vectors 'pSSA-K' (Accession No. KCTC10536BP, Nov. 7, 2003, Korean Collection for Type Cultures, Korea Research Institute of Bioscience and Biotechnology (KRIBB). #52, Oun-dong, Yusong-ku, Taejon, 305-333, Republic of Korea, *Escherichia coli* DH5@/pSSa-K) and 'pSSA-H'(Accession No. KCTC10537BP, Nov. 7, 2003, Korean Collection for Type Cultures, Korea Research Institute of Bioscience and Biotechnology (KRIBB). #52, Oun-dong, Yusong-ku, Taejon, 305-333, Republic of Korea, *Escherichia coli* DH5@/pSSA-H) for the production of multiple stress tolerant plants containing oxidative stress inducible peroxidase promoter, tobacco etch virus (TEV) leader sequence, multiple stress tolerant genes, transit peptide sequence for chloroplast targeted expression, CaMV 35S transcription terminator, antibiotics resistant gene and T-DNA boarder sequence.

The present invention also provides a transgenic plant transformed with the above pSSA-K or pSSA-H expression vector.

The present invention also provides a preparation method for multiple stress tolerant transgenic plants comprising the following steps:

i) Preparing expression vectors for plant transformation comprising SWPA2 promoter, SOD gene and APX gene;

ii) Preparing a transformant by inserting the expression vector above into a plant or culture cells;

iii) Culturing the transformant above; and iv) Preparing a transgenic plant by regeneration after tissue-culturing the transformant.

Hereinafter, the present invention is described in detail.

The present invention provides recombinant expression vectors pSSA-K and pSSA-H for the production of multiple stress tolerant plants containing oxidative stress inducible peroxidase promoter, tobacco etch virus (TEV) leader sequence, transit peptide sequence for chloroplast targeted expression, multiple stress tolerant genes, CaMV 35S transcription terminator, antibiotics resistant gene and T-DNA boarder sequence.

In a preferred embodiment of the present invention, nucleotide sequence of SWPA2 (sweetpotato peroxidase anionic 2) promoter, represented by SEQ. ID. No 11, is preferably used as oxidative stress inducible peroxidase promoter originated from sweetpotato, and nucleotide sequence of SOD gene represented by SEQ. ID. No 12 and nucleotide sequence of APX gene represented by SEQ. ID. No 13 are preferably used as multiple stress tolerant genes.

The present inventors deposited pSSA-K and pSSA-H, expression vectors for the production of multiple stress tolerant plants, prepared by the inventors as the above at Korean Collection for Type Cultures (KCTC) of Korea Research Institute of Bioscience and Biotechnology (KRIBB), on Nov. 7, 2003. The accession number of pSSA-K expression vector is KCTC 10536BP and the accession number of pSSA-H expression vector is KCTC 10537BP.

SWPA2 promoter is an oxidative stress inducible promoter isolated from sweetpotato (*Ipomoea batatas*) by the present inventors, which is very useful for the development of stress tolerant plants and plant cell lines for the production of other useful products (Korean Patent Publication No: 2001-51095; International Publication No: WO 01/31018 (applied on Oct. 28, 2000); Kim, et al., Plant Mol. Biol., 51: 831-838, 2003). Precisely, as a peroxidase promoter highly expressed in culture cells, SWPA2 is a gene whose expression is induced by oxidative stress. In particular, the gene is specifically highly expressed in the late log phase in sweetpotato suspension culture cells and transformed tobacco suspension culture cells (International Publication No: WO 01/31018). The promoter showed at least 30-fold higher activity than CaMV 35S promoter in transient assay with GUS protein using tobacco protoplast. The promoter is not expressed in leaves of a plant under normal conditions, but is expressed when they get oxidative stresses such as ozone, low temperature, wound, etc (Kim, et al., Plant Mol. Biol., 51: 831-838, 2003). Thus, SWPA2 promoter of the present invention can be effectively used for the development of environmental stress tolerant plants and for the production of useful products using the transformed plant cells.

SWPA2 promoter of the present invention effectively induces the expression of a target gene by stress. SWPA2 promoter of the invention includes factors recognizing outward stress generated by ABA (abscisic acid), methyl jasmonate, wound, hypoxia, oxygen free radical, heat or nitrogen. Based on this characteristic of the promoter, SWPA2 promoter is useful for the construction of chimeric gene structure in which DNA sequence having a promoter activity is linked to a structural gene to work with the promoter sequence effectively. Such chimeric gene structure enables the expression of a valuable factor under any environmental stress by the control of SWPA2 promoter owing to the linkage between a structural gene involved in the production of valuable factors and SWPA2 promoter, so that it can be effectively used for the preparation of transformants for the production of useful products. In addition, when multiple stress tolerant genes are given as a structural gene to the chimeric gene structure, a transformant having stress tolerance can be produced.

SOD gene used in this invention is separated from over 30 kinds of plants in general. And, in particular, CuZnSOD gene (mSOD1) isolated first from cultured cells of cassava (*Manihot esculenta*) selected as SOD high-production cell line was used in the present invention (Mol. Gen. Genet. 262: 807-814, 1999) along with APX gene isolated from pea (Free Rad. Biol. Med. 23: 473-479, 1997).

In the preferred embodiment of the present invention, the present inventors constructed pSA vector by connecting SWPA2 promoter represented by SEQ. ID. No 15 to pRW20 vector, into which mSOD1 gene represented by SEQ. ID. No 16 was inserted to prepare pSS vector (see FIG. 1). Then, SWPA2pro-TEV-TP-SOD-35S transcription terminator structure of pSS vector was inserted into an expression vector for plant transformation containing hygromycin resistant gene or kanamycin resistant gene, followed by the insertion of SWPA2pro-TEV-TP-APX-35S transcription terminator structure separated from pSA vector thereto. As a result, pSSA-K and pSSA-H expression vectors for the production of multiple stress tolerant plants were constructed (see FIG. 2). pSSA-K and pSSA-H expression vectors above include SWPA2 promoter, mSOD1, APX gene, tobacco etch virus (TEV) leader sequence, transit peptide for chloroplast targeted expression and CaMV 35S transcription terminator in addition to hygromycin resistant gene or kanamycin resistant gene respectively, which makes the selection of multiple stress tolerant plants transformed with the vectors easy.

The present invention also provides a multiple stress tolerant plant transformed with pSSA-K or pSSA-H expression vector. All kind of plants are possibly used for the production of transgenic plants, but soybean, barley, corn, potato, sweetpotato or tall fescue is preferred and especially potato, sweetpotato or tall fescue is more preferred.

The present invention provides a multiple stress tolerant transgenic plants prepared by transforming with recombinant expression vector for the production of multiple stresses tolerant plants containing SWPA2 promoter, SOD gene and APX gene so as to express the SOD gene and APX gene massively in plants.

In the preferred embodiment of the present invention, pSSA-K or pSSA-H expression vector constructed above was inserted into a plant, preferably in soybean, barley, corn, potato, sweetpotato or tall fescue and more preferably in potato, sweetpotato or tall fescue, to express SOD gene and APX gene. Particularly, the present inventors inserted the above expression vectors into young leaves or petiole sections of potato, sweetpotato or tall fescue by using *Agrobacterium tumefaciens* EHA105 or by means of particle bombardment, in order to prepare transformants. The resultant transformants were tissue-cultured to induce regeneration into plants (see FIG. 3A, FIG. 4A and FIG. 5A). Genomic DNA was extracted from each regenerated transgenic potato, sweetpotato or tall fescue, from which SWPA2 promoter or APX gene was amplified by PCR to confirm the insertion of SWPA2 promoter or APX gene in plant genome (see FIG. 3B, FIG. 4B and FIG. 5B). Genomic DNA was also extracted from each transgenic plant after confirmation of the successful transformation by PCR, which was transferred to membrane. Southern blot hybridization was performed using SWPA2 promoter or APX gene to re-confirm the insertion of SWPA2 promoter or APX gene in plant genome (see FIG. 3C, FIG. 4C and FIG. 5C).

In order to confirm the stress resistance of a transgenic plant transformed with pSSA-K or pSSA-H expression vector, the present inventors induced oxidative stress like applying methyl viologen (MV) or hydrogen peroxide in leaf discs of transformed potato, sweetpotato or tall fescue or plant themselves, and then investigated ionic conductivity (see FIGS. 6, 7, 9, 10 and 11), visual damage (see FIG. 8A and FIG. 11C), photosynthetic efficiency (see FIG. 11A), dry weight of leaf (see FIG. 8B and FIG. 11B) and chlorophyll content (see FIG. 8C). As a result, it was confirmed that transgenic plants transformed with pSSA-K or pSSA-H expression vector of the present invention showed excellent tolerance against oxidative stress tolerance than non-transformed plants. It was also confirmed that the transgenic plant of the present invention could maintain normal conditions under other stresses like high temperature (see FIG. 13B~FIG. 14B), low temperature (see FIG. 15A and FIG. 15B) or $SO_2$ stress (see FIG. 16 and FIG. 17).

The present invention also provides a transgenic plant transformed with the above pSSA-K or pSSA-H expression vector.

The present invention also provides a preparation method for multiple stress tolerant transgenic plants comprising the following steps:

i) Preparing expression vectors for plant transformation comprising SWPA2 promoter, SOD gene and APX gene;

ii) Preparing a transformant by inserting the expression vector above into a plant or culture cells;

iii) Culturing the transformant above; and iv) Preparing a transgenic plant by regeneration after tissue-culturing the transformant.

At this time, pSSA-K or pSSA-His preferred as an expression vector, and any plant can be used as the plant or culture cells above but soybean, barley, corn, potato, sweetpotato or tall fescue is preferred, and potato, sweetpotato or tall fescue is more preferred.

The transformant above can be prepared by the conventional plant transformation method (Horsch, et al., Cold Spring Harb Symp Quant Biol., 50: 433-7, 1985; Rogerset, et. al., 1986), but particle bombardment is preferably used to produce a transformant herein.

In the preferred embodiment of the present invention, pSSA-K or pSSA-His used as an expression vector since transgenic plants transformed with the vector can be easily selected because the vector contains SWPA2 promoter, SOD gene, APX gene, transit peptide sequence for chloroplast targeted expression, tobacco etch virus (TEV) leader sequence, CaMV 35S transcription terminator, and hygromycin or kanamycin resistant gene.

MODE FOR INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Construction of pSSA-K and pSSA-H, Expression Vectors for Multiple Stress Tolerant Genes The present inventors constructed a vector by ligating cDNA (GenBank accession number AF170297, Lee, et al., *Mol. Gen. Genet.*, 262: 807-814, 1999) coding CuZnSOD (CuZn superoxide dismutase, mSOD1) of cassava represented by SEQ. ID. No 16 and cDNA coding APX (ascorbate peroxidase; Randy, et al., *Free Rad. Biol. Med.*, 23: 473-479, 1997) of pea represented by SEQ. ID. No 17 to oxidative stress inducible SWPA2 promoter (Korean Patent Publication No: 2001-51095; International Publication No: WO 01/31018) represented by SEQ. ID. No 15.

Figure 1:
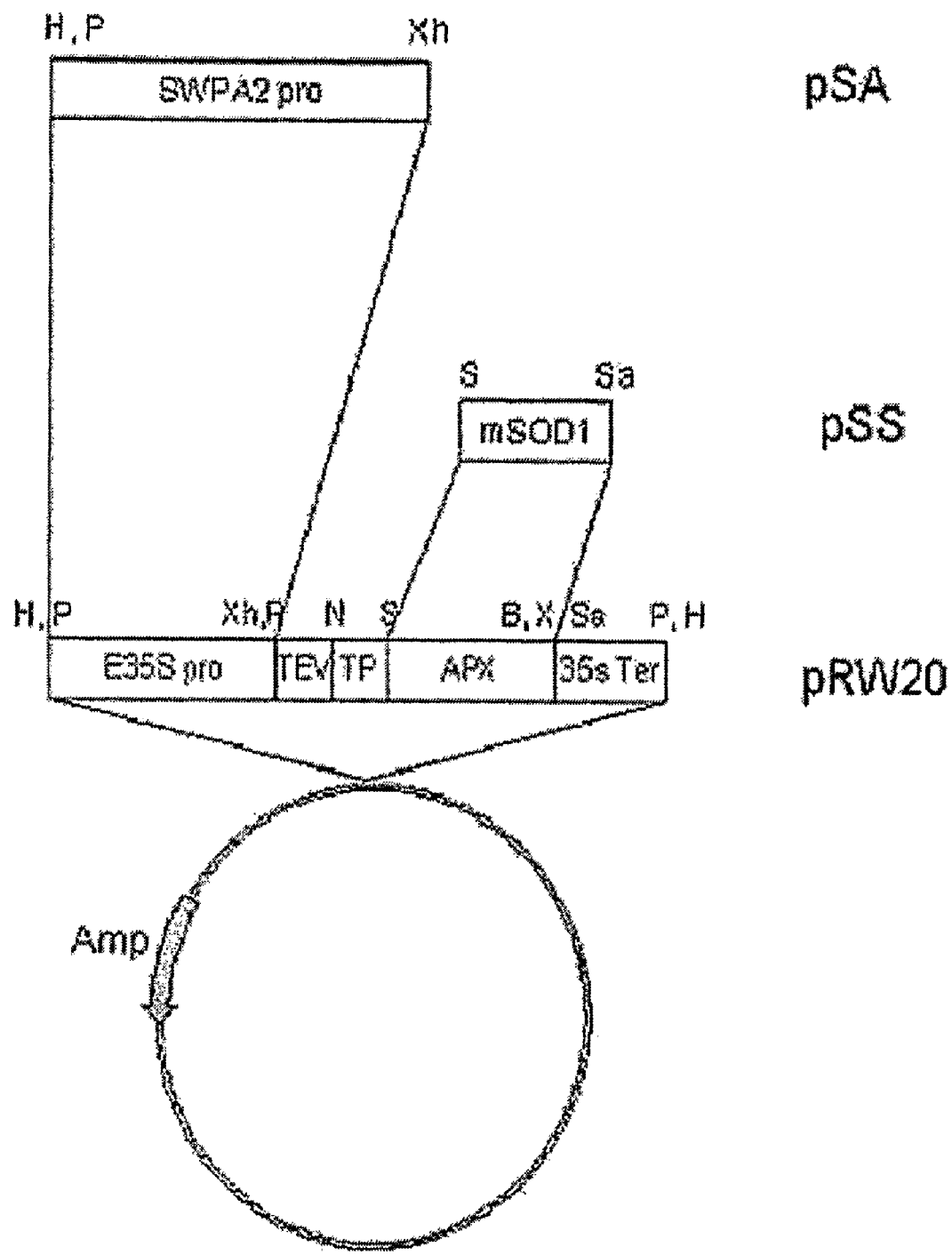
FIG. 1 is a schematic diagram showing the producing procedure of a vector of the present invention expressing SOD (superoxide dismutase) and APX (ascorbate peroxidase) genes simultaneously.

Particularly, PCR was performed using primers each represented by SEQ. ID. No 1 and No 2 at 94° C. for 1 minute, at 51° C. for 1 minute, at 72° C. for 1 and half minute (this cycle was repeated 30 times) to amplify SWPA2 promoter sequence. And the amplified SWPA2 promoter sequence was cloned into pGEM-T Easy plasmid vector (Promega, USA) according to the manufacturer's protocol. And the nucleotide sequence of the vector was analyzed to confirm whether or not the target sequence of SWPA2 promoter was amplified correctly. The nucleotide sequence of the primer had Hind III and Xho I restriction sites. Thus, it was possible to isolate SWPA2 promoter sequence from pGEM-T Easy plasmid vector by treating Hind III and Xho I. And, pRW20 vector (Allen, et al., *Free Rad. Biol. Med.*, 23: 473-479, 1997) constructed for the delivery of APX (ascorbate peroxidase) of pea to chloroplasts was digested with the same enzymes to eliminate enhanced CaMV 35S promoter. Then, the SWPA2 promoter sequence isolated earlier was ligated to the vector, resulting in the construction of pSA vector (FIG. 1).

In order to replace APX gene in pSA vector with mSOD1 gene, PCR was performed using primers each represented by SEQ. ID. No 3 and No 4 at 94° C. for 1 minute, at 57° C. for 1 minute and at 72° C. for 1 minute (this cycle was repeated 30 times) to amplify mSOD1 gene. And the amplified mSOD1 was cloned into pGEM-T Easy plasmid vector (Promega, USA) according to the manufacturer's protocol. Nucleotide sequence analysis was performed to confirm whether or not the target mSOD1 gene was correctly amplified. The nucleotide sequence of the primer had Sal I and Sac I restriction sites. Thus, mSOD1 gene was isolated from pGEM-T Easy plasmid vector in which mSOD1 gene was cloned earlier by the treatment of Sal I and Sac I. Then, the isolated mSOD1 gene was inserted into the above pSA vector digested with the same restriction enzymes. And the resultant vector was named pSS vector (FIG. 1).

Figure 2:
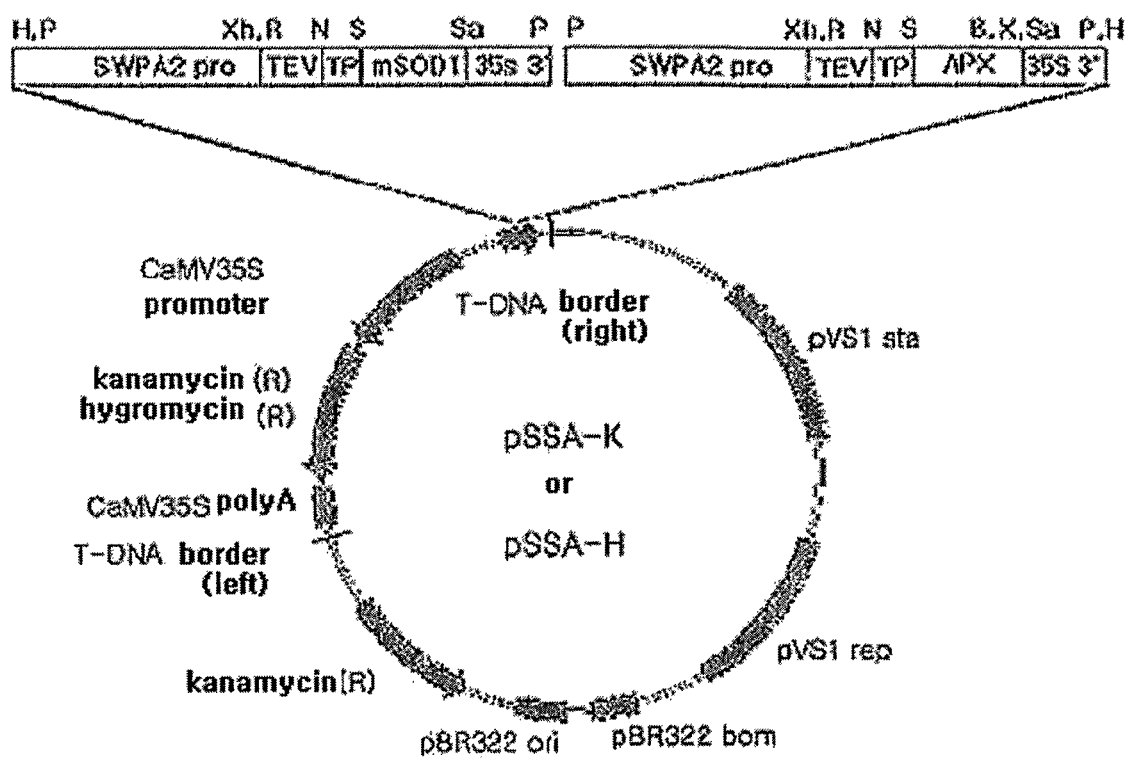
FIG. 2 is a schematic diagram showing a recombinant expression vector for the production of multiple stress tolerant plant containing SOD and APX genes.

Lastly, pSSA-K and pSSA-H, vectors for plant transformation, were constructed to transform SOD and APX simultaneously by using pCAMBIA1300 plasmid (Center for Application of Molecular Biology to International Agriculture, Australia) containing hygromycin resistant gene and pCAMBIA2300 plasmid (Center for Application of Molecular Biology to International Agriculture, Australia) containing kanamycin resistant gene. Particularly, the above pSS vector was digested with Hind III to obtain about 2.0 kb sized DNA fragment, which was inserted into pCAMBIA1300 plasmid and pCAMBIA2300 plasmid, pre-digested with the same restriction enzymes. pSA was also digested with Pst I to obtain 2.3 kb sized DNA fragment, which was inserted into the above plasmids, resulting in the construction of expression vectors having both SOD and APX genes, pSSA-K vector (the DNA fragment was inserted into pCAMBIA2300) and pSSA-H vector (the DNA fragment was inserted into pCAMBIA1300) (FIG. 2). The present inventors deposited pSSA-K and pSSA-H constructed by the inventors as the above at Korean Collection for Type Cultures (KCTC) of Korea Research Institute of Bioscience and Biotechnology (KRIBB), on Nov. 7, 2003. The accession number of pSSA-K expression vector is KCTC 10536BP and the accession number of pSSA-H expression vector is KCTC 10537BP. In FIG. 1 and FIG. 2, SWPA2 pro: oxidative stress inducible promoter, E35S pro: enhanced CaMV 35S promoter, TEV: tobacco etch virus (TEV) leader sequence, TP: signal sequence of pea CuZnSOD (Cu.Zn superoxide dismutase), 35S 3': CaMV 35S transcription terminator, Amp: antibiotics (ampicillin) resistant gene, H: Hind III, P: Pst I, Xh: Xho I, R: EcoR 1, N: Nco 1, S: Sal 1, B: BamH 1, X: Xba 1, and Sa: Sac 1.

A transgenic potato plant was prepared by inserting the expression vector for plant transformation constructed above (pSSA-K or pSSA-H) into *Agrobacterium tumefaciens* EHA105 (Hood, et al., *Trans. Res.*, 2: 208-218, 1993) according to An's method (An, *Meth. Enzymol.*, 153: 292-305, 1987).

And also, plasmid DNA (pSSA-K vector) was separated from *E. coli* by using Plasmid Maxi kit provided by Qiagen Co (U.S.A), then used for the transformation of sweetpotato by particle bombardment explained in the below example 3.

EXAMPLE 2

Preparation of a Transgenic Potato Transformed with pSSA-K Expression Vector

<2-1> Preparation of a Transgenic Potato Plant

The present inventors prepared a transgenic potato plant by co-culturing leaf discs of a potato plant and *Agrobacterium tumefaciens* EHA105 containing pSSA-K vector constructed in the above example 1.

Particularly, the potato plant (*Solanum tuberosum* L.) used for the transformation herein was prepared by culturing Superior, the most world-widely cultivated variety, and Atlantic, a variety for processing, in an incubator. The potato plant was cultured in MS medium (Murashige and Skoog, *Physiol. Plant.*, 15: 473-497, 1962) supplemented with 3% sucrose with the light condition of 16-hour light/8 hour dark under cool-white fluorescence (40 μmol·m$^{-2}$·sec$^{-1}$) in a 25° C. incubating room. After culturing 2 weeks, petiole and the second or the third leaf on the upper part of shoot, were separated and used as materials for plant transformation.

5 ml of LB medium (bacto peptone 10 g/l, yeast extract 5 g/l and NaCl 10 g/l) supplemented with 50 mg/l of kanamycin was inoculated with Agrobacteria, followed by culture at 28° C. in a shaking incubator for one day. 100 μl of the Agrobacteria culture solution and leaf and petiole discs of a potato plant were completely mixed in a petri dish containing 10 ml of MS basic liquid medium, followed by co-culture at 25° C. under darkness for 2 days. Agrobacteria were washed with MS basic liquid medium, and then moisture in leaf and petiole disc obtained from co-cultivated potato plant was eliminated with sterilized filter paper. Then leaf and petiole discs were placed on the selection medium (MS medium containing 2 mg/l of zeatin, 0.01 mg/l of NAA (naphthaleneacetic acid), 0.1 mg/l of GA3 (gibberellin), 300 mg/l of claforan and 100 mg/l of kanamycin). The discs were transferred to a fresh new medium every three weeks, followed by sub-culture. The generation of kanamycin resistant shoot and callus was observed after 3-4 weeks from the beginning of culture.

Figure 3:
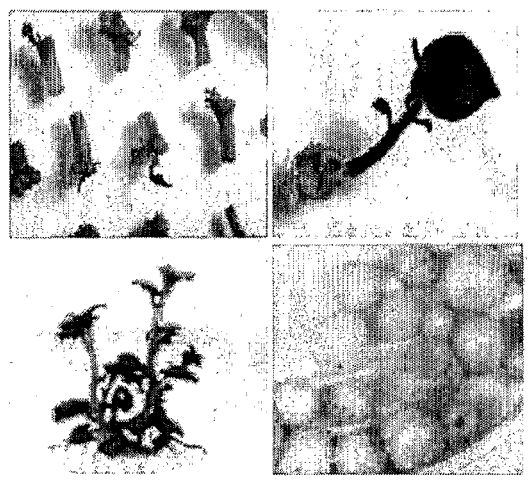
FIG. 3A is a photograph showing the morphology of each organ of a regenerated plant after tissue culturing of a transgenic potato (Variety: Superior) having kanamycin resistance produced by using a recombinant expression vector (pSSA-K) for the production of multiple stress tolerant plant.
FIG. 3B is an electrophoresis photograph confirming the amplification of SWPA2 promoter in transgenic potato plant transformed with the expression vector of the present invention (pSSA-K vector) by PCR using primers represented by SEQ. ID. No 1 and No 2.
FIG. 3C is a Southern blot photograph confirming that SOD and APX genes are presented on genome of transgenic potato plant prepared by using the expression vector of the present invention (pSSA-K vector)
Figure 3:
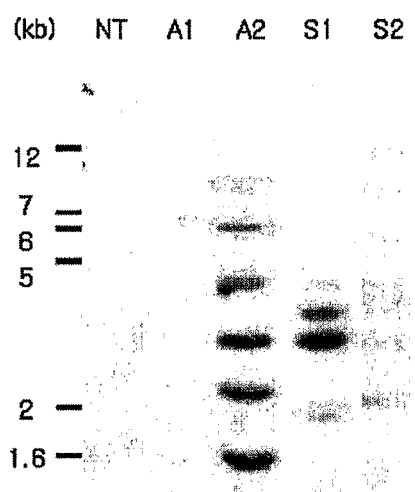
Figure 3:
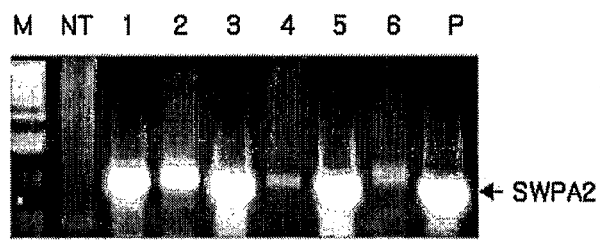

When one or two leaves were out, the shoot was transferred to a root inducing medium (MS basic medium containing 300 mg/l of claforan and 100 mg/l of kanamycin) to induce roots. Roots were well induced from the shoot, and the small plant with roots was taken out of the culture container to be exposed outside for 4-5 days (acclimated in incubating room), then transferred to horticultural bed soil flowerpot, followed by further culture in an incubator (FIG. 3A). As a result, microtuber was formed in a potato plant grown in the incubator (FIG. 3A). There was no significant difference in morphology between a transgenic potato plant harboring a foreign gene and a non-transformed one. In the meantime, when petioles were used as transformation material, more shoots were formed than when leaf discs were used for the transformation. Though, most of them were not transformed, confirmed by PCR.

<2-2> Confirmation of a Transformant by PCR and Southern Blot

In order to investigate whether or not the potato plant prepared in the above example 2-1 was rightly transformed, regenerated plants were selected first from the medium supplemented with kanamycin, and then PCR was performed with specific primers for SWPA2 promoter represented by SEQ. ID. No 5 and No 6 at 94° C. for 1 minute, at 53° C. for 1 minute and at 72° C. for 1 minute (this cycle was repeated 30 times) to amplify SWPA2 promoter sequence, leading to the selection of a transformant (FIG. 3B). As a result, 0.5 kb fragment was amplified from the plant harboring a foreign gene, suggesting that SWPA2 promoter was inserted. In FIG. 3B, M: molecular size marker, NT: non-transformed potato plant, 1-5: kanamycin resistant potato plant, and P: positive control DNA.

Southern blotting was performed with randomly selected potato plants that were confirmed by PCR. Precisely, genomic DNA was extracted from leaves of each Atlantic and Superior plants that were growing in an incubator by using Dneasy Plant Maxi kit (QIAGEN Co.). 30 μg of genomic DNA was digested with restriction enzyme EcoRI, followed by electrophoresis on agarose gel. The genomic DNA on the gel was transferred to Zeta Probe membrane (Bio-Rad Co.), followed by hybridization of the transferred DNA with 0.5 kb DNA fragment of SWPA2 promoter sequence labeled with $^{32}$P as a probe. Upon completion of hybridization, membrane was washed and then exposed on X-ray film to detect a band. As a result, while no band was observed in a non-transgenic control plant, more than 3 bands were observed in transformed Atlantic and Superior plants, meaning SWPA2 promoter was stably inserted in the genome of the potato (FIG. 3C). In FIG. 3C, NT: non-transformed potato plant, A1 and A2: transformed Atlantic plants, and S1 and S2: transformed Superior plants.

EXAMPLE 3

Preparation of a Transgenic Sweetpotato Plant by Using pSSA-K Expression Vector

<3-1> Preparation of a Transgenic Sweetpotato Plant

The present inventors transformed sweetpotato embryogenic callus by particle bombardment using pSSA-K vector constructed in the above example 1.

Particularly, embryogenic callus of sweetpotato (*Ipomoea batatas* Lam.; Variety: Yulmi) being cultivated in Korea was used as transformation material in this invention. More precisely, embryogenic callus of sweetpotato was induced and maintained to establish sweetpotato plant regeneration system (Kwon, et al., *Korean J. Plant Biotechnol.*, 29: 189-192, 2002).

Figure 4:
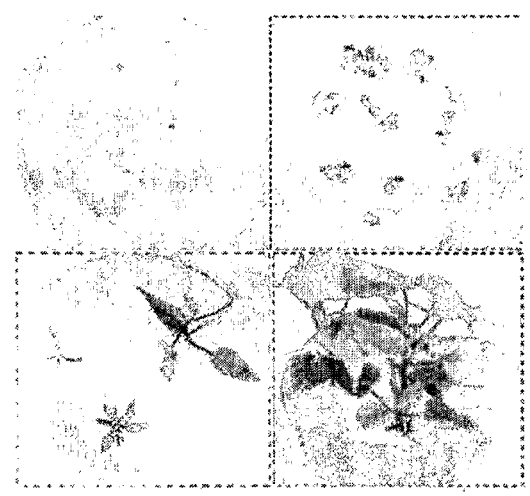
FIG. 4A is a photograph showing the morphology of each organ of a regenerated plant after tissue culturing of kanamycin resistant transgenic sweetpotato (Variety: Yulmi) produced by using the expression vector of the present invention (pSSA-K vector)
FIG. 4B is an electrophoresis photograph confirming the amplification of SWPA2 in transgenic sweetpotato plant transformed with the expression vector of the present invention (pSSA-K vector) by PCR using primers represented by SEQ. ID. No 1 and No 2.
FIG. 4C is a Southern blot photograph confirming that SOD and APX genes are presented on genome of transgenic sweetpotato plant transformed with the expression vector of the present invention (pSSA-K vector)
Figure 4:
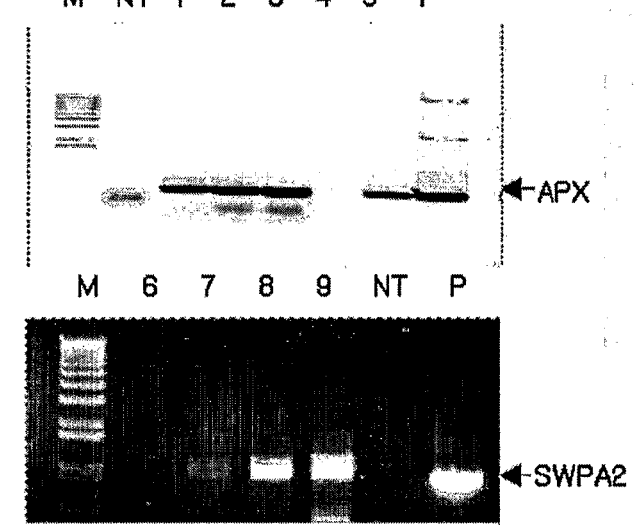
Figure 4:
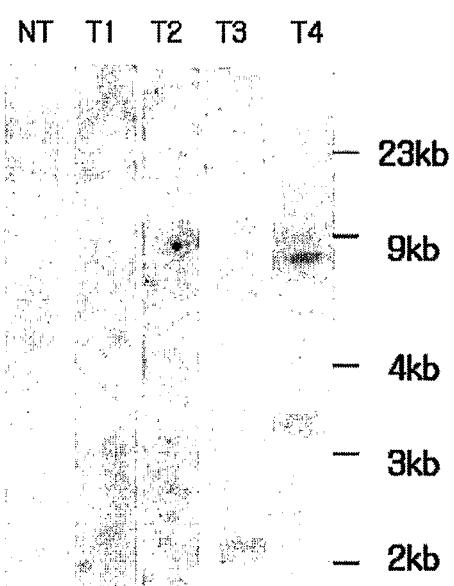

The embryogenic callus was cut by cell clusters into 1-2 mm in diameter. The cell clusters were placed within a central circle in 2 cm in diameter on MS solid medium supplemented with 1 mg/l of 2,4-dichlorophenoxy acetic acid (2,4-D), which was cultured for one day, followed by particle bombardment (FIG. 4A). More precisely, plasmid DNA of pSSA-K vector for plant transformation constructed in the example 1 was prepared. Then, gold particles (1 μm in diameter) were coated with the plasmid DNA, followed by particle bombarding using PDS-1000/He particle delivery system (BioRad Co.) under 1,100 psi pressure with 9 cm distance.

After particle bombarding, the plant was cultured in a 25° C. dark place for 3 days, then kanamycin resistant embryogenic callus was selected from MS selection medium supplemented with 1 mg/l of 2,4-D and 100 mg/l of kanamycin. The selection proceeded for 5-6 months, at 3 weeks interval, during sub-culture. The kanamycin resistant embryogenic callus was transferred to MS basal medium supplemented with only 100 mg/9 of kanamycin without 2,4-D. And the embryogenic callus was converted to somatic embryo in incubator under 40 $\mu mol \cdot m^{-2} \cdot sec^{-1}$ cool-white fluorescent condition at 25° C., leading to regeneration to a plant (FIG. 4A).

<3-2> Confirmation of a Transformant by PCR and Southern Blotting

In order to confirm whether or not a transgenic sweetpotato plant prepared in the above example 3-1 was correctly transformed, regenerated plant was selected first from kanamycin containing medium. PCR was performed with the plant using specific primers for SWPA2 promoter represented by SEQ. ID. No 7 and No 8 or specific primers for APX gene represented by SEQ. ID. No 9 and No 10, at 94° C. for 1 minute, at 56° C. for 1 minute and at 72° C. for 1 minute (this cycle was repeated 30 times) to amplify SWPA2 promoter or APX gene, followed by electrophoresis for the selection of a transformant (FIG. 4B). As a result, 1 kb DNA fragment was amplified from the plant in which a foreign gene was inserted when specific primers for SWPA2 promoter were used, and about 0.5 kb DNA fragment was amplified therefrom when specific primers for APX gene were used, suggesting that SWPA2 or APX gene was stably inserted. In FIG. 4B, M: molecular size marker, NT: non-transformed sweetpotato plant, 1-9: kanamycin resistant sweetpotato plant, and P: positive control DNA.

Southern blotting was performed with randomly selected sweetpotato plants confirmed by PCR. Particularly, genomic DNA was extracted from leaves of sweetpotato plant that was being grown in an incubator by using Dneasy Plant Maxi kit (QIAGEN Co.). 30 μg of the obtained DNA was digested with restriction enzyme EcoR I, followed by electrophoresis on agarose gel. The genomic DNA on the gel was transferred to Zeta probe membrane (Bio-Rad Co.). The transferred DNA was hybridized 0.5 kb DNA fragment, which was a part of mSOD1, labeled with $^{32}P$ as a probe. Upon completion of hybridization, the membrane was washed and then exposed on X-ray film to find a band. As a result, more than 2 copies of mSOD1 were stably inserted in kanamycin resistant sweetpotato plant, while no band was observed in a control plant (FIG. 4C). In FIG. 4C, NT: non-transformed sweetpotato plant, and T1-T4: transformed sweetpotato (Variety: Yulmi) plant.

EXAMPLE 4

Preparation of a Transgenic Tall Fescue Plant By Using pSSA-H Expression Vector

<4-1> Preparation of a Transgenic Tall Fescue Plant

The present inventors co-cultured *Agrobacterium tumefaciens* EHA105 containing pSSA-H vector (plasmid DNA) constructed in the above example 1 and tall fescue section to induce transformation of the same.

Figure 5:
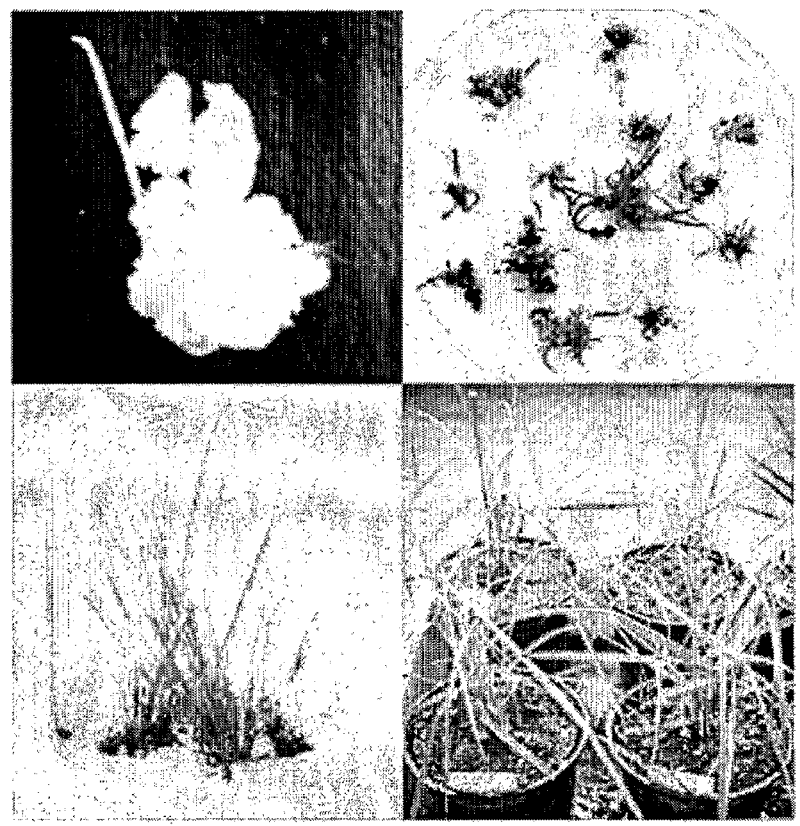
FIG. 5A is a set of photographs showing a regenerated plant obtained from tissue culture of hygromycin resistant transgenic tall fescue prepared by using the expression vector of the present invention (pSSA-H vector)
FIG. 5B is a PCR photograph confirming that SOD and APX genes are presented on genome of transgenic tall fescue plant transformed with the expression vector of the present invention (pSSA-H vector)
FIG. 5C is a Southern blot photograph confirming that SOD and APX genes are presented on genome of transgenic tall fescue plant transformed with the expression vector of the present invention (pSSA-H vector)
Figure 5:
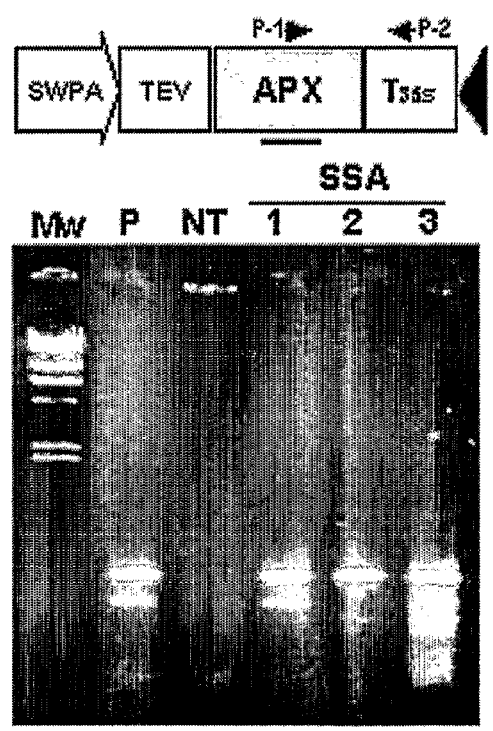
Figure 5:
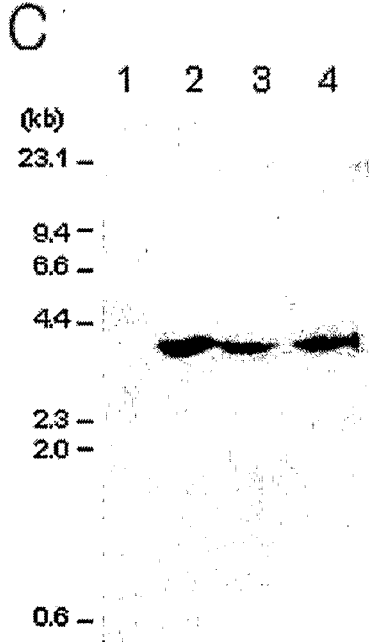

Particularly, Kenturky-31, mainly cultured as animal feed, was used for the transformation of tall fescue (*Festuca arundinacea* Schreb.). For the preparation of callus for the transformation of tall fescue, seeds were sterilized and seed coats were eliminated therefrom. Then, the seeds were cultured in a callus inducing medium [MS medium containing 9 mg/l of 2,4-D, 0.1 mg/l of BA (benzyl adenine), 30 g/l of sucrose, 5 g/l of gelite] for 4 weeks to induce callus. Agrobacteria culture solution, which was cultured in YEP liquid medium (10 g/9 of bacto-peptone, 10 g/l of yeast extract and 5 g/l of NaCl) supplemented with 50 mg/l of kanamycin at 28° C. for 2 days, was centrifuged to obtain bacteria cells. Then, the solution was suspended in callus indufing liquid medium supplemented with 100 μM acetosyringone, 20 mg/l of ascorbic acid and 5 mg/l of silver nitrate ($AgNO_3$) until $OD_{600}$ was reached to 1. The callus was dipped in Agrobacteria suspension for 30 minutes under vacuum to induce infection. Then, the surplus Agrobacteria were eliminated and callus was transferred to a co-culture medium (callus inducing medium containing 100 μM acetosyringone, 20 mg/l of ascorbic acid and 5 mg/l of silver nitrate), followed by further culture at 28° C. for 3 days. The infected callus was transferred to after-culture medium (MS medium containing 5 mg/l of 2,4-D, 1 mg/l of BA, 140 mg/l of FeNaEDTA, 70 mg/l of myo-inositol, 25 mM proline, 0.4 mM thioproline, 50 mM $K_2SO_4$, 2 g/l of yeast extract, 30 g/9 of sucrose and 5 g/9 of gelite), followed by further culture for 1 week. Then, the callus was cultured again in the primary selection medium (N6 basic medium containing 0.5 mg/l of 2,4-D, 2 mg/9 of BA, 140 mg/9 of FeNaEDTA, 70 mg/l of myo-inositol, 25 mM proline, 0.4 mM thioproline, 50 mM $K_2SO_4$, 2 g/9 of yeast extract, 30 g/9 of sucrose, 5 g/l of gelite and 25 mg/l of hygromycin) for 2 weeks. The survived callus in the primary selection medium and regenerated shoots were transferred to the second selection medium (first selection medium+50 mg/l of hygromycin), followed by culture for 3 weeks to regenerate the transgenic plant. The shoots of the regenerated plant were cut off and then explanted in ½ MS solid medium supplemented with 50 mg/l of hygromycin and 30 g/l of sucrose to induce the development of roots. Only those individuals showing hygromycin resistance were selected. After acclimation, those individuals were transplanted into a flowerpot and cultivated (FIG. 5A).

<4-2> Confirmation of a Transformant by PCR

PCR and Southern blotting were performed using genomic DNA to confirm whether or not a target gene was inserted into a transgenic tall fescue plant prepared in the above example 4-1. At that time, genomic DNA extracted from a tall fescue plant showing a strong resistance in a selection medium containing hygromycin and from a control that is wild type tall fescue grown up from normal germination were used as templates. And also, a forward primer represented by SEQ. ID. No 11 and a reverse primer represented by SEQ. ID. No 12 were selected among nucleotide sequences of pSSA-H vector and used for PCR to confirm the insertion of a target gene by amplifying a specific nucleotide sequence region of the expression vector. PCR was performed with 30 cycles of 94° C./1 minute, 52° C./1 minute, and 72° C./1 minute. As a result, about 0.5 kb sized target fragment was amplified, suggesting that APX gene was correctly inserted. In FIG. 5B, Mw: molecular size marker, P: positive control DNA, NT: non-transformed tall fescue plant, 1-3: hygromycin resistant tall fescue plants.

Each genomic DNA was extracted from a hygromycin resistant tall fescue plant and a wild type tall fescue plant that was grown up from normal germination, and then digested with restriction enzyme Hind III, followed by electrophoresis on agarose gel. The DNA was transferred to nylon membrane. Southern blotting was performed using a part of APX gene (426 bp) amplified by PCR using primers represented by SEQ. ID. No 13 and No 14 as a probe. As a result, one specific band was observed in the tall fescue plant having a strong hygromycin resistance. On the other hand, no band was detected in a control plant (FIG. 5C). In FIG. 5C, 2, 3 and 4: transformed tall fescue plants.

EXAMPLE 5

Environmental Resistance of SSA Transgenic Plant

<5-1> Oxidative Stress Resistance

<5-1-1> Oxidative Stress Resistance of Leaf Discs of a Potato Plant

Figure 6:
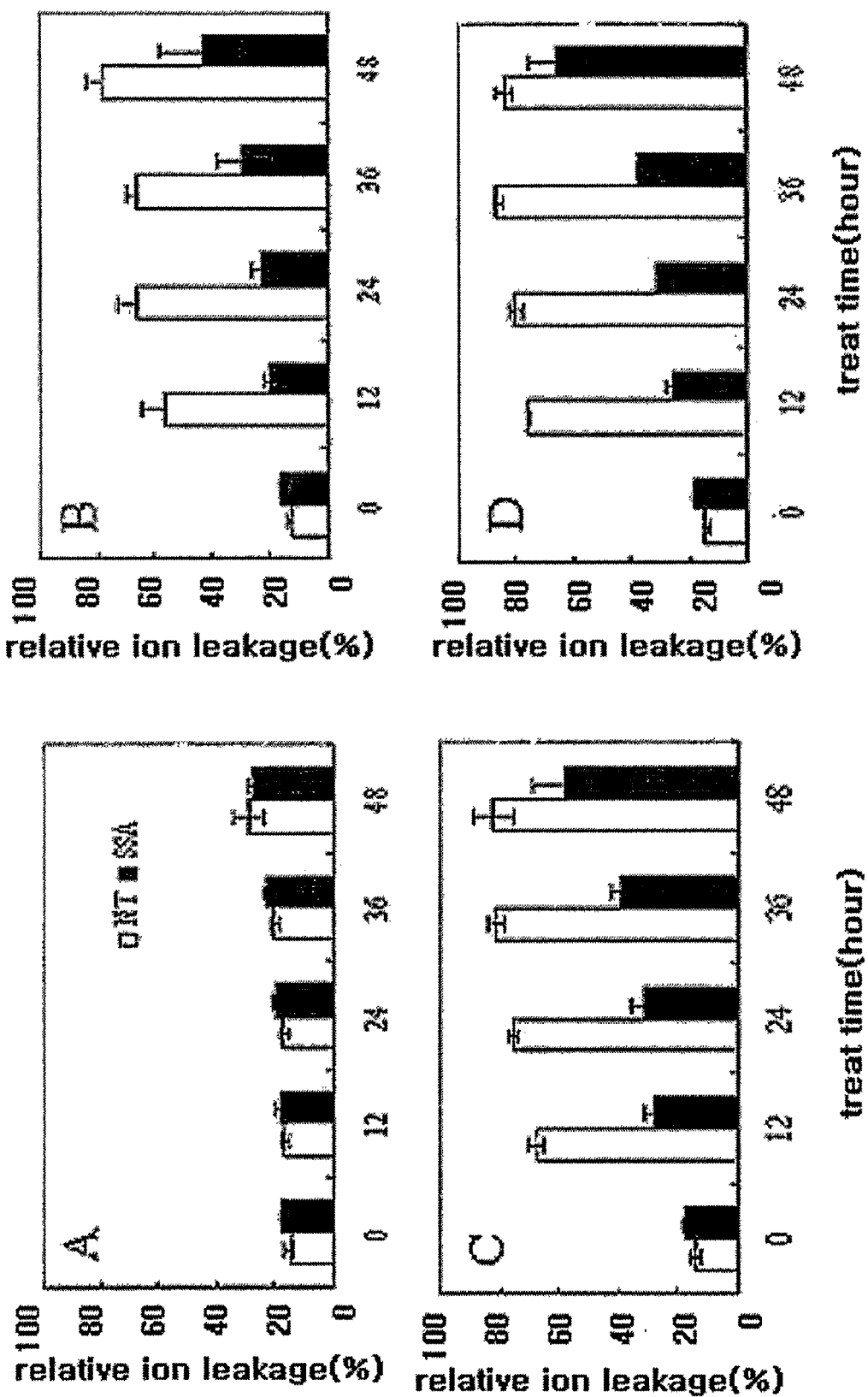
FIG. 6 is a set of graphs showing the membrane damage in leaf discs of NT and SSA potato plants after treating them in methyl viologen (MV) solution with different concentrations (0, 3, 5 and 10 μM), which was measured by investigating ionic conductivities in the solution.

In order to investigate resistance against oxidative stress of SSA transgenic potato (Variety: Atlantic), a non-transformed plant (NT plant) and SSA plant were grown in a greenhouse. 10 leaf discs (8 mm in diameter) were taken from a leaf of 7 week old plant (the $5^{th}$ or the $7^{th}$ leaf from the top), which were floated on 5 my of 0.4 M sorbitol solution containing 0, 3, 5 and 10 μM of methyl viologen (MV). They were cultured for 12 hours under darkness to let them absorb MV. After that, they were incubated again for 48 hours under the light. Then, ionic conductivity of the solution was measured by using conductivity meter (Orion, Model 162), leading to the measurement of leaf damage (FIG. 6). FIG. 6A shows the result of the treatment with 0 μM of MV, 6B shows the result of the treatment with 3 μM of MV, 6C shows the result of the treatment with 5 μM of MV and 6D shows the result of the treatment with 10 μM of MV. In case of non-treatment, ionic conductivities of NT and SSA plant leaves were maintained steady as 20% for 48 hours. In case of MV treatment, electrical conductivity of the solution containing SSA plant leaf discs was much lower than that of the solution containing NT plant leaf discs. Serious leaf damage began to be observed in NT plants from the 12 hours after treatment of 3, 5, and 10 μM of MV. In particular, over 80% cell damage was observed after 48 hours after treatment. However, cell damage in SSA plants was just about 40% for 36 hours after treatment. Those results indicate that SSA plant has twice as strong resistance as NT plant does. That is, a transgenic potato plant in which SOD and APX are expressed simultaneously in chloroplasts has increased resistance against oxidative stress caused by MV. In FIG. 6, NT: non-transformed plant and SSA: plant harboring pSSA-K vector.

<5-1-2> Oxidative Stress Resistance of a Potato Plant

Figure 7:
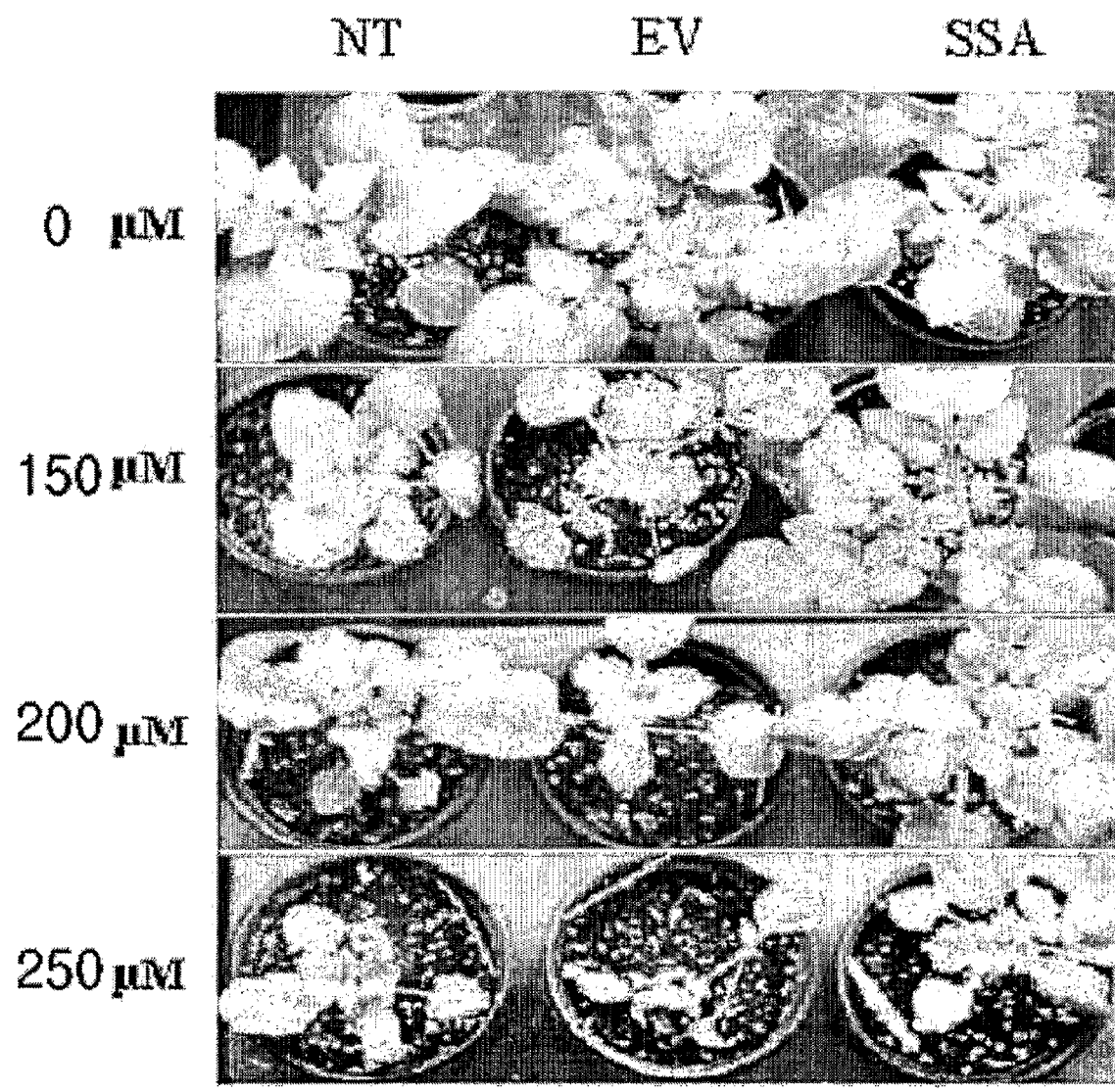
FIG. 7 is a set of photographs showing the MV resistance levels in potato plants after 5 days from spray with MV solution at different concentration of 0, 150, 200 and 250 μM.

In order to investigate resistant capacity against oxidative stress of a plant, NT plant, EV plant (a plant harboring pCAMBIA2300 vector) and SSA plant were treated with 70 μl of MV solution (containing 0.1% tween 20) at different concentrations of 0, 150, 200 and 250 μM by using a spray booth (Model SB-6, DeVries Manufacturing, Hollandale, Minn.). 5 days after spraying MV solution, visual damage in plant leaves was investigated. As a result, when 150 μM of MV solution was sprayed, partial wilting was observed in leaves of NT and EV plants, but no damage was observed in SSA plant. The damage in NT and EV plant leaves was increased with the increase of MV concentration. The leaves of the plants were damaged by 90% with the concentration of 250 μM, but the leaves of SSA plant were just slightly damaged (FIG. 7). In FIG. 7, NT: non-transformant, EV: plant harboring pCAMBIA2300 vector and SSA: potato plant harboring pSSA-K vector.

Figure 8:
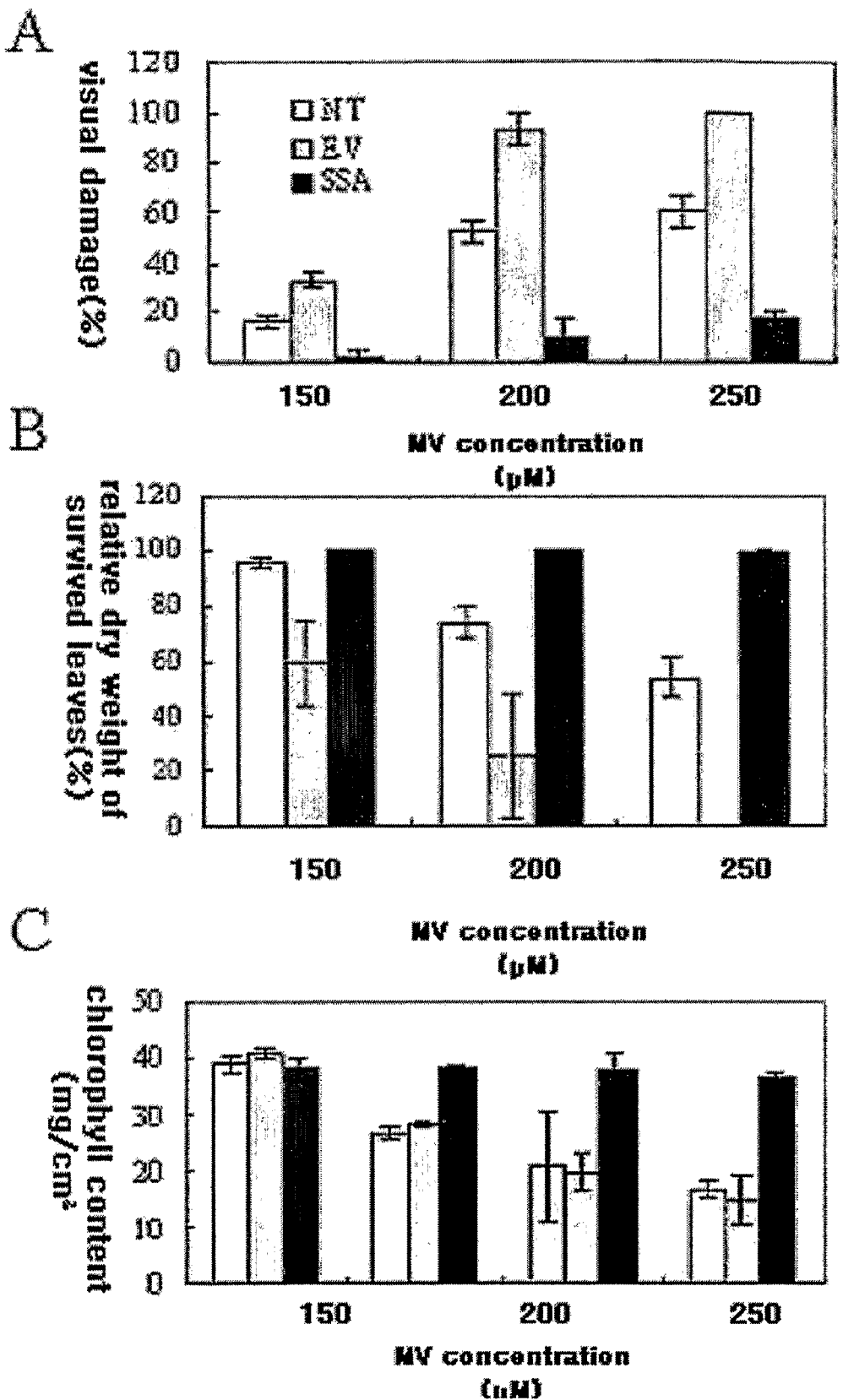
FIG. 8 is a set of graphs showing the visual damage in leaves of a potato plant (A), relative dry weight of survived leaves (B), and chlorophyll content (C) after 5 days from spray with MV solution at different concentrations of 0, 150, 200 and 250 μM.

Visual damage, dry weight of leaves and chlorophyll content were measured to investigate MV resistance of SSA plant. When 150 μM of MV solution was sprayed onto each NT plant and EV plant leaves, 20-40% leaf damage was observed in each plant but the damage in SSA plant was less than 20% (FIG. 8A). In the meantime, dry weight of survived normal leaves of NT and EV plants after MV treatment was decreased with the increase of MV concentration. The dry weight of leaves was 50% decreased when 250 μM of MV solution was treated (FIG. 8B). On the contrary, in the case of transgenic plants, dry weight of leaves survived after the treatment was almost the same as that of non-treated leaves, regardless of MV concentration. The results of investigation on chlorophyll content were similar to those of dry weight measurement. Chlorophyll contents of non-treated plant and MV treated transgenic plant were about 40 mg/cm$^2$ (FIG. 8C). In FIGS. 8A-8C, NT: non-transformant, EV: plant harboring pCAMBIA2300 vector and SSA: potato plant harboring pSSA-K vector.

<5-1-3> Oxidative Stress Resistance of Leaf Discs of a Sweetpotato Plant

Figure 9:
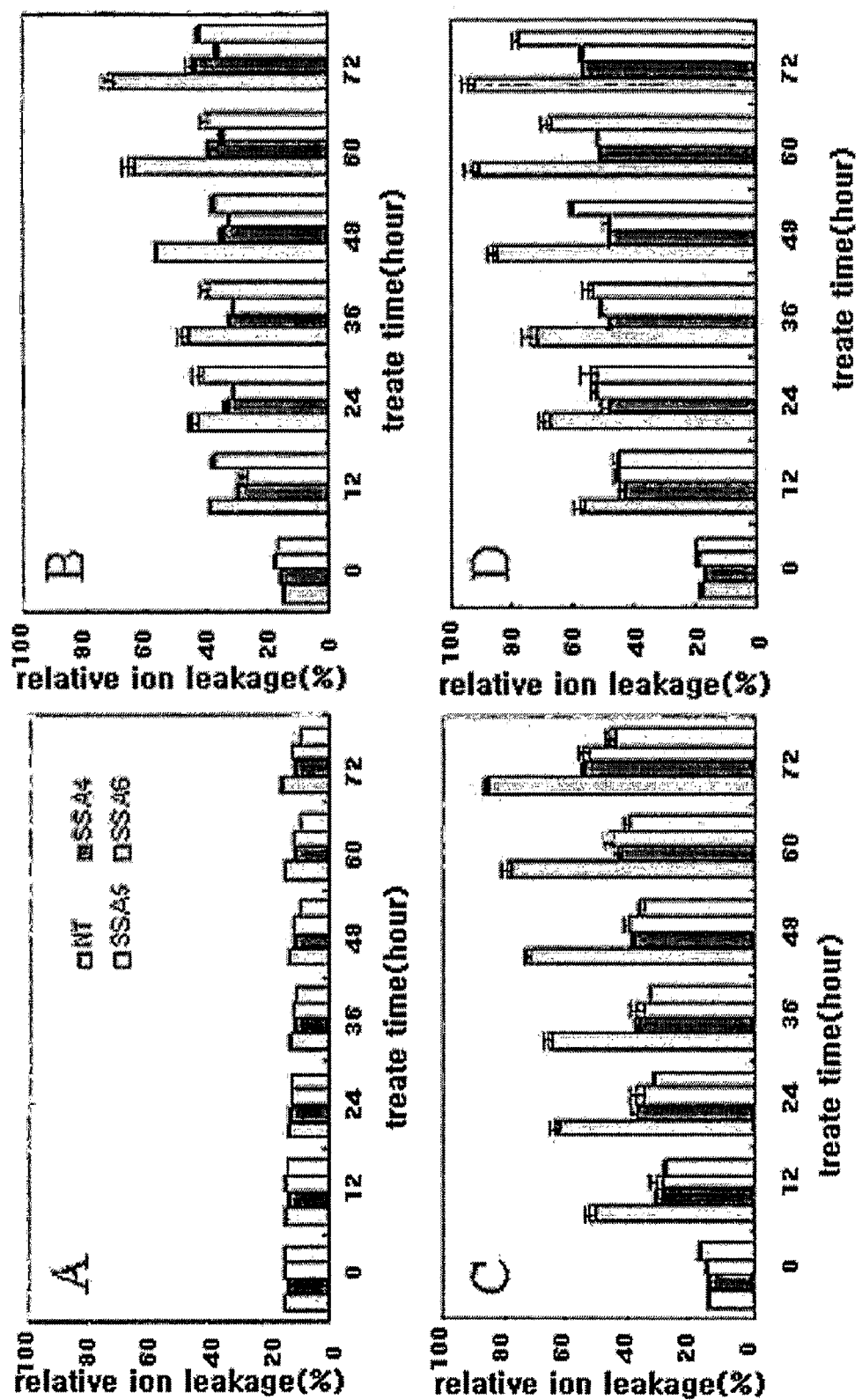
FIG. 9 is a set of graphs showing the membrane damage in discs of sweetpotato leaves of NT and SSA plants treated with different concentrations of MV solution (0, 2.5, 5 and 10 μM) for 72 hours, which was measured by investigating ionic conductivities in the solution.

In order to investigate oxidative stress resistance of SSA transgenic sweetpotato (Variety: Yulmi), three of each non-transgenic plant (NT plant) and SSA plant were grown in a greenhouse. 10 leaf discs (8 mm in diameter) were taken from a leaf (the third or the forth leaf from the top) of a plant, which had been grown for 8 weeks, and then treated with 0, 2.5, 5, and 10 μM of methyl viologen (MV) by the same method as used in example 5-1-1. After MV treatment, damage in leaf disc resulted from the treatment of MV at different concentrations was measured (FIG. 9). FIG. 9A shows the damage by the treatment of 0 μM of MV, B shows the damage by the treatment of 2.5 μM of MV, C shows the damage by the treatment of 5 μM of MV and D shows the damage by the treatment of 10 μM of MV. Electronical conductivity of the solution containing leaf discs of SSA plant was very low, comparing to that of the solution containing leaf discs of NT plant. While over 50% cell damage was observed in leaf discs of NT plant after 12 hours from MV treatment, cell damage was less than 30% in leaf discs of SSA plant. In particular, the treatment of 5 μM of MV caused 45% cell damage in leaf discs of SSA plant, comparing to NT plant. In FIG. 9, NT: non-transformed plant and SSA: a sweetpotato plant harboring pSSA-K vector.

<5-1-4> Oxidative Stress Resistance of a Sweetpotato Plant

Figure 10:
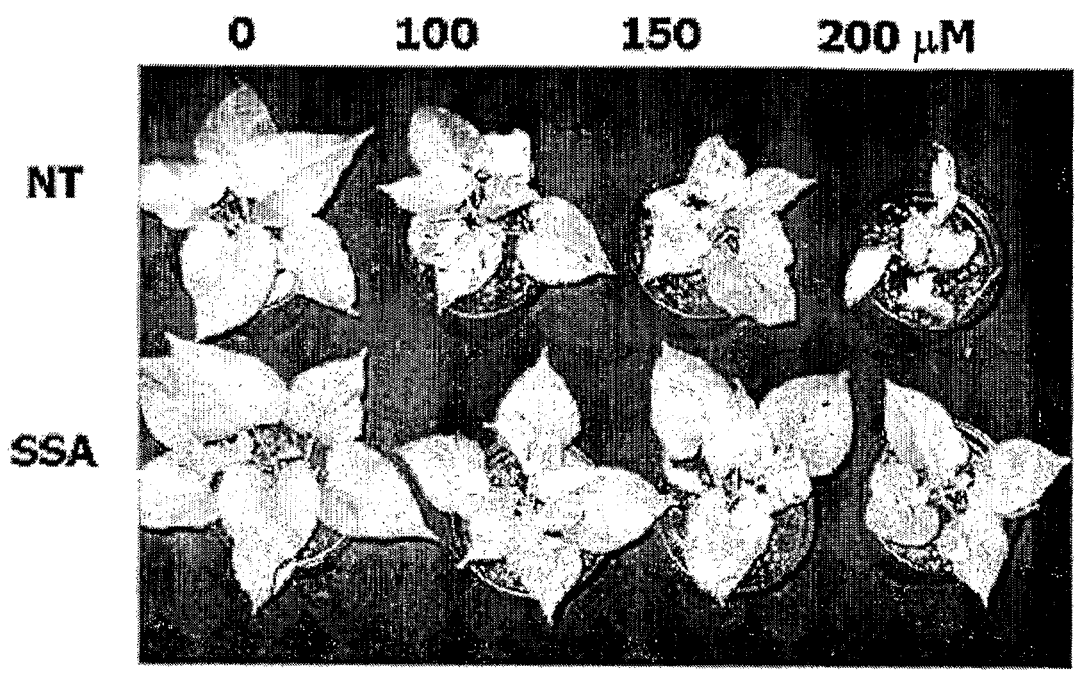
FIG. 10 is a set of photographs showing the MV resistance levels in sweetpotato plants after 5 days from spray with MV solution at different concentration of 0, 100, 150 and 200 μM.

In order to investigate resistant capacity against oxidative stress of a sweetpotato plant, NT plant and SSA plant that were grown for 4 weeks in a greenhouse were treated with 70 ml of MV solution (containing 0.1% tween 20) at different concentrations of 0, 100, 150 and 200 μM in the analogy to the procedure as described in example 5-1-2. 5 days after MV treatment, visual damage in leaves of a plant was observed. When 100-150 μM of MV was sprayed, leaves of NT plant were witted with albinism. However, only partial damage was observed in leaves of SSA plant. In the meantime, when 200 μM of MV was sprayed, leaves of NT plant were almost wilted, but albinism was observed only in some parts of leaves of SSA plant (FIG. 10). In FIG. 10, NT: non-transformant, EV: a sweetpotato plant harboring pCAMBIA2300 vector and SSA: a sweetpotato plant harboring pSSA-K vector.

Figure 11:
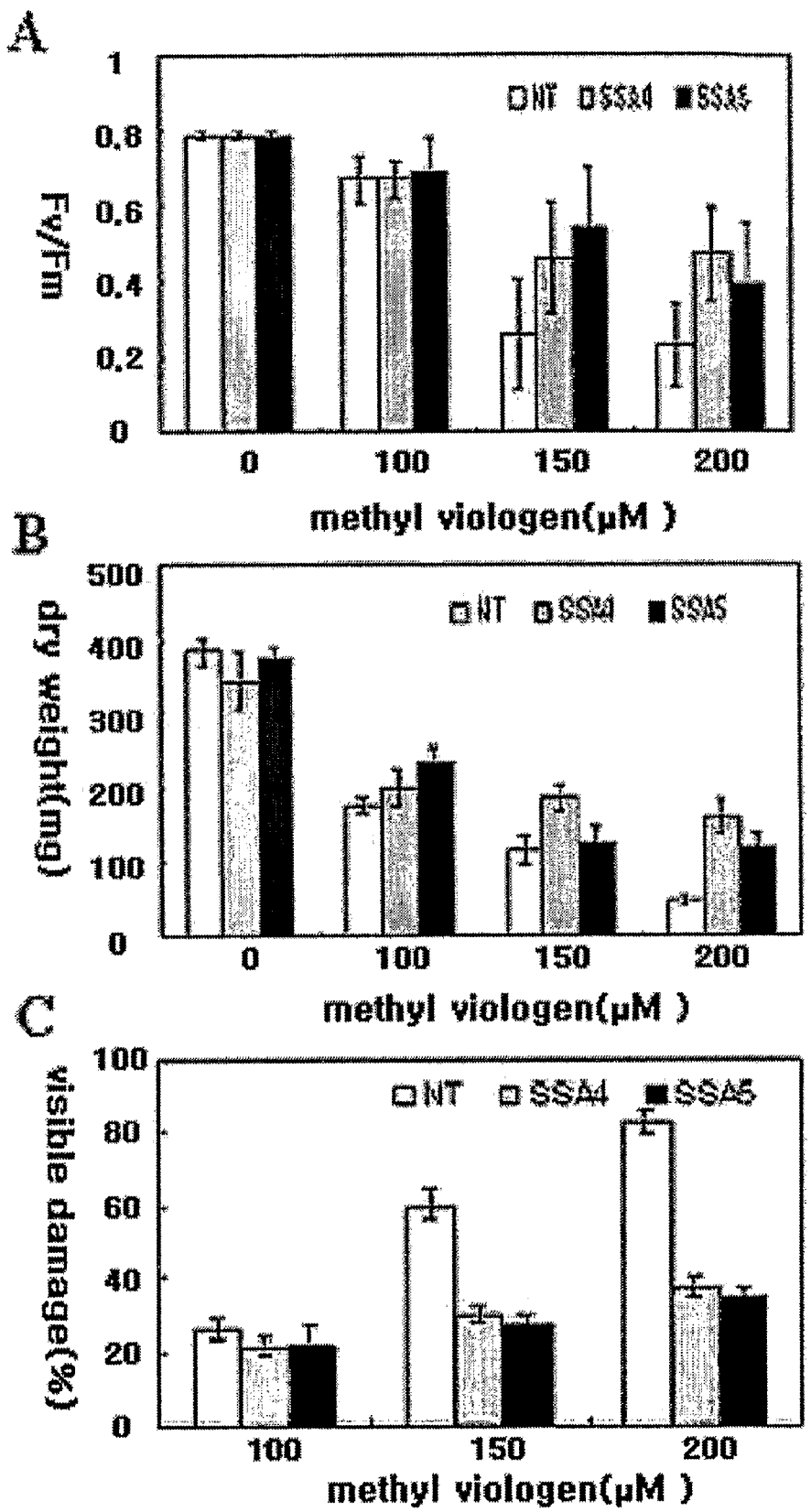
FIG. 11 is a set of graphs showing the photosynthetic efficiency (A), relative dry weight of survived leaves (B) and visual damage in leaves (C) of sweetpotato plant after 5 days from spray with MV solution at different concentrations of 0, 100, 150 and 200 μM.

MV resistance of SSA plant was also investigated by measuring photosynthetic efficiency, dry weight of leaves and visual leaf damage. The third leaf from the top of a plant was taken to measure photosynthetic efficiency 2 days after MV treatment. When 100 μM of MV was sprayed, photosynthetic efficiencies in NT and SSA plants were a little decreased to 0.7, comparing to before the treatment (FIG. 11A). When 150 and 200 μM of MV was sprayed, photosynthetic efficiency was over 0.4, which was twice as high as that of NT plant. Dry weight of leaves was also measured 5 days after MV treatment. As a result, dry weights of NT plant and SSA plant were about 400 mg before MV treatment, but dry weight of leaves in NT plant was decreased with the increase of MV concentration. Precisely, when 200 μM of MV was treated, dry weight was 90% reduced, comparing to MV-non treating plant. In the meantime, dry weight of SSA plant leaves was 60% reduced, showing three-fold higher resistance than NT plant (FIG. 11B). And also, visual damage in a plant was observed 5 days after MV treatment. As a result, there was not much difference in visual damage between NT plant and SSA plant treated with 100 μM of MV. However, leaves of NT plant were 85% damaged by 200 μM of MV and leaves of SSA plant were 40% or less damaged, meaning that MV resistance in SSA plant became doubled, comparing to that of NT plant (FIG. 11C). In FIGS. 11A-11C, NT: non-transformant, SSA4 and SSA5: sweetpotato plants harboring pSSA-K vector.

<5-1-5> Oxidative Stress Resistance of Leaf Discs of a Tall Fescue Plant

Figure 12:
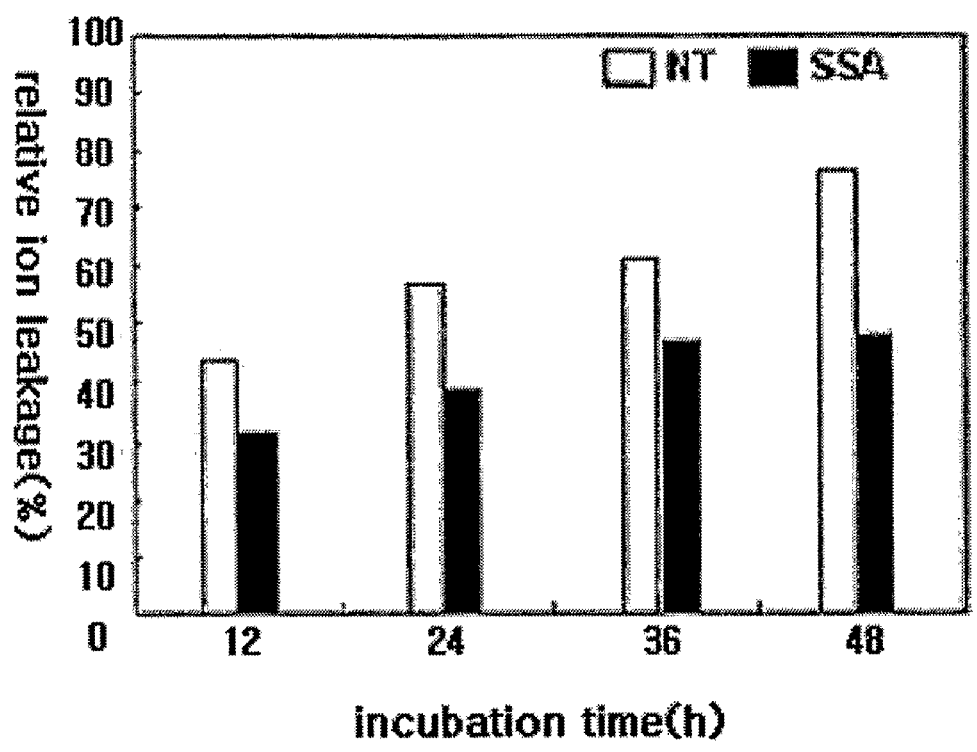
FIG. 12 is a set of graphs showing the membrane damage in leaf discs of tall fescue plant treated with 5 μM of MV solution (A) and 50 mM of $H_2O_2$ solution (B)
Figure 12:
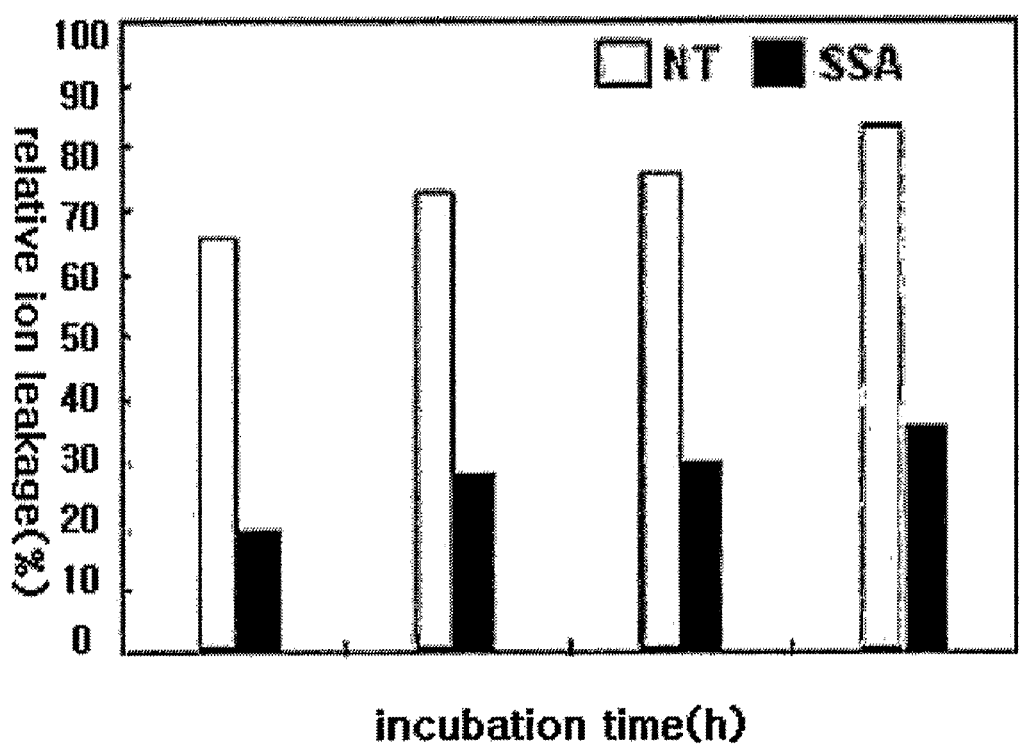

In order to investigate oxidative stress resistance of SSA transgenic tall fescue plant, non-transformed plant (NT plant) and SSA plant were grown in a greenhouse. 10 leaf discs (8 mm in diameter) were taken from a leaf of a plant at 7 weeks (the $5^{th}$-the $7^{th}$ leaf from the top), and then floated on 5 ml of 0.4 M sorbitol solution supplemented with 5 μM of methyl viologen (MV), followed by culture for 12 hours under darkness to let the discs absorb MV. After the treatment with darkness, they were cultured again for 48 hours under the light. Then, ionic conductivity of the solution was measured by using electrical conductivity meter (Orion, Model 162) to measure leaf damage (FIG. 12A). Electrical conductivity of the solution containing the leaf discs of SSA plant was very low, comparing to that of NT plant, after MV treatment. From 12 hours after MV treatment, the leaf discs of NT plant showed serious damage, and from the 48 hours after treatment, cell damage was over 75% in NT plant. Cell damage in SSA plant was 40% until 36 hours after MV treatment. Those results indicate that SSA plant has two-fold higher resistance against oxidative stress induced by MV than NT plant. Leaf-discs of a tall fescue plant that was grown by the same method as above were treated with 50 mM of hydrogen peroxide, followed by further incubation for 48 hours. Ionic conductivity of the solution was measured by an electrical conductivity meter to investigate leaf damage (FIG. 12B). After hydrogen peroxide treatment, cell damage in SSA plant was very low, comparing to NT plant. More precisely, dell damage was over 65% in NT plant from the 12 hours after treatment. On the contrary, cell damage was less than 25% in SSA plant up to 48 hours from the treatment. In conclusion, SSA plant had at least 2.6-fold higher resistance against oxidative stress caused by hydrogen peroxide than NT plant. From the above result was confirmed that SSA plant had higher resistance against oxidative stresses caused by MV and hydrogen peroxide than NT plant. That is, transgenic tall fescue plants in which SOD and APX were expressed simultaneously in chloroplast had increased resistance against oxidative stress caused by MV and hydrogen peroxide. In FIGS. 12A-12B, NT: non-transformed plant and SSA: a plant harboring pSSA-H vector.

<5-2> Resistance Against Stress by Temperature

<5-2-1> Heat Stress Resistance of Leaf Discs of a Potato Plant

Figure 13:
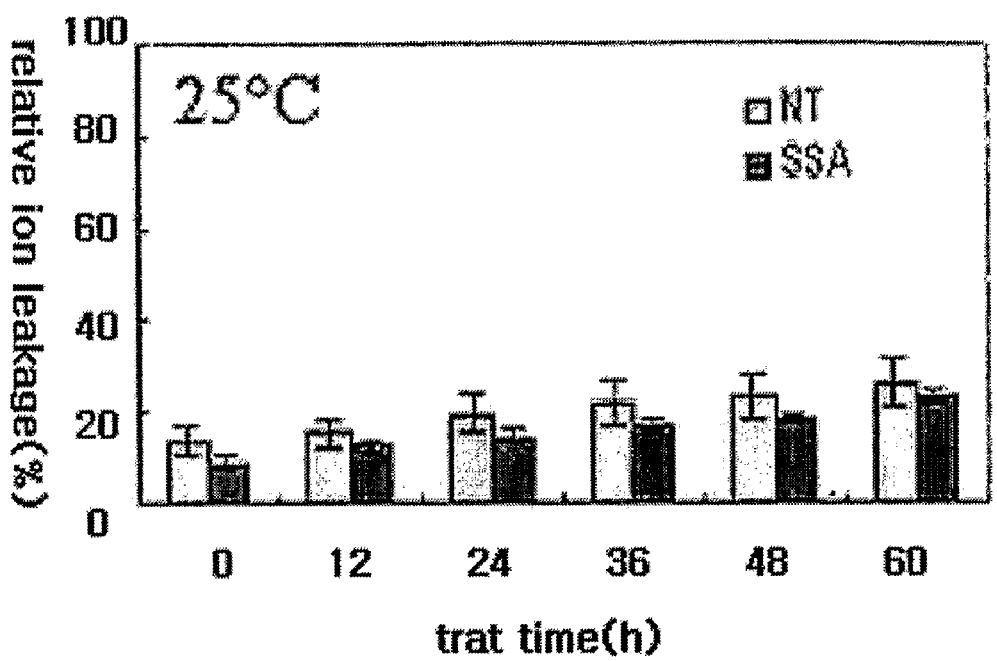
FIG. 13 is a set of graphs showing the high-temperature resistance observed in leaf discs of a potato plant, precisely, ionic conductivity in membrane was investigated after the treatment at high temperature (25° C. (A) and 37° C. (B)) for 60 hours.
Figure 13:
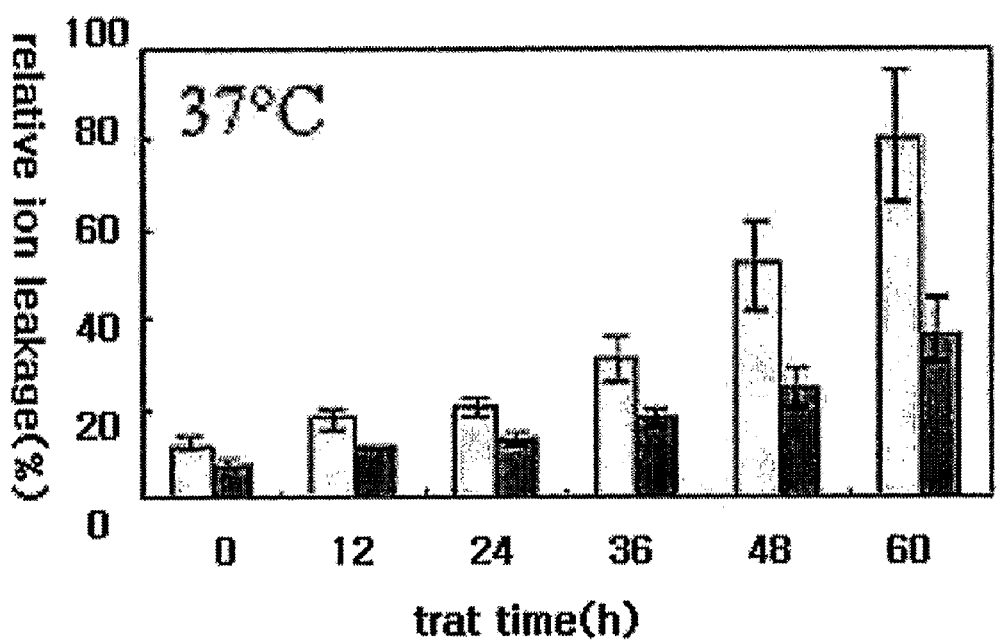

In order to investigate heat stress (high temperature) resistance of SSA transgenic potato plant (Variety: Atlantic), NT plant (non-transformed plant) and a SSA plant were grown in a greenhouse. 10 leaf discs (8 mm in diameter) were taken from a leaf of 7 week old plant (the $5^{th}$-the $7^{th}$ leaf from the top) and floated on 5 ml of 0.4 M sorbitol solution, followed by incubate at 37° C. for 60 hours. A control plant was incubated under the same conditions except 25° C. temperature. Ionic conductivity of the solution was measured every 12 hours to investigate leaf damage. Ionic conductivities of NT plant and SSA plant were steadily maintained for 60 hours (FIG. 13A), when stress by high temperature was not given (25° C. treating group). However, stress resistance against high temperature in SSA plant was significantly increased when stress by high temperature at 37° C. was given (FIG. 13B). The stress resistance in SSA plant began to be detected after 12 hours from the high temperature treatment, and ionic conductivities at 36 and 48 hour were 42% and 52%, respectively. And after 60 hours from the treatment, the resistance became doubled. In FIG. 13A and FIG. 13B, NT: non-transformed plant and SSA: plant harboring pSSA-K vector.

<5-2-2> Heat Stress Resistance of a Potato Plant

Figure 14:
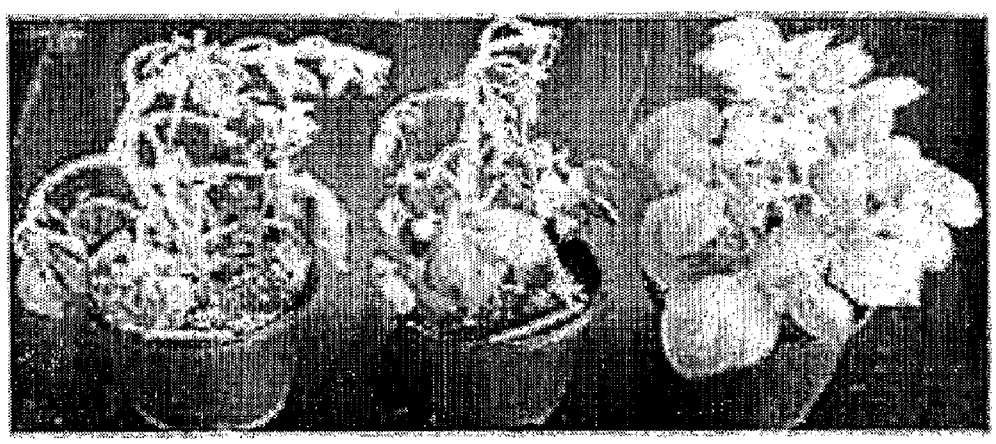
FIG. 14 is a set of photographs and a graph showing the result of the investigation on high temperature resistance of a potato plant. Precisely, visual damage (A) resulted from heat-treatment at 42° C. for 10 hours, and photosynthetic efficiency (B) after treatment at 42° C. for 10 hours, 20 hours and after 3 hour-recovery at 25° C. after the treatment of high temperature were investigated.
Figure 14:
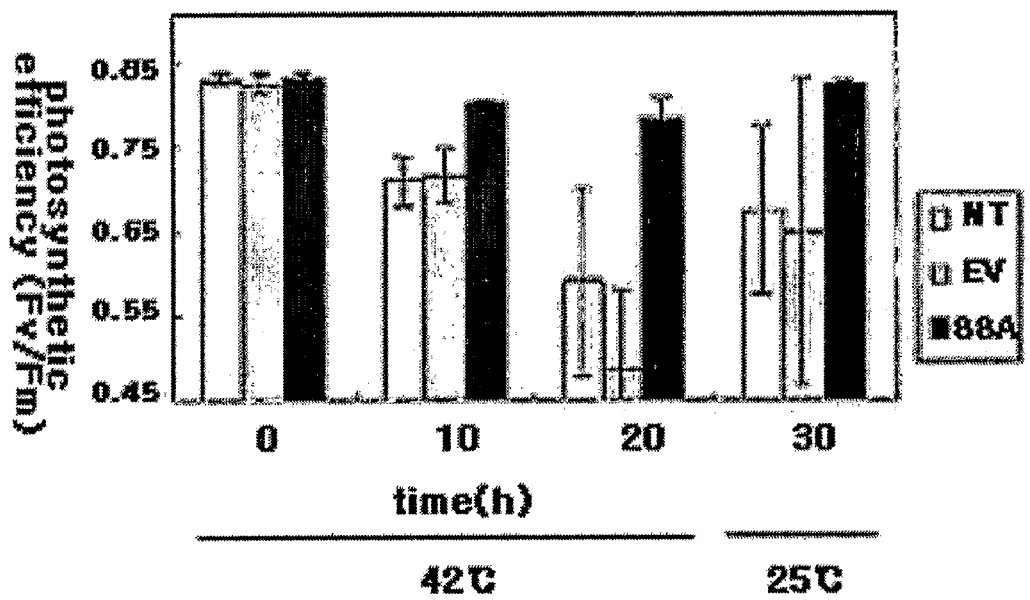

In order to investigate resistance against stress caused by high temperature of a transgenic potato (Variety: Atlantic), NT plant, EV plant and SSA plant of potato plant grown for 4 weeks (Variety: Atlantic) were exposed on the temperature of 42° C. for 10 hours. As a result, NT plant and EV plant were wilted, but SSA plant survived healthy (FIG. 14A). Photosynthetic efficiencies were compared between before the high temperature treatment and after the treatment. As a result, high temperature treatment for 10 and 20 hours reduced photosynthetic efficiency in NT plant by 15% and 30% respectively, but the high temperature treatment even for 20 hours in SSA plant reduced photosynthetic efficiency only by 6% (FIG. 14B). After the high temperature treatment, plants were recovered at 25° C. for 3 hours. As a result, photosynthetic efficiencies in NT plant and EV plant were 50% recovered, comparing to those of before treatment. In the meantime, photosynthetic efficiency in SSA plant was almost recovered to the original photosynthetic efficiency. In FIG. 14A and FIG. 14B, NT: non-transformant, EV: plant harboring pCAMBIA2300 vector and SSA: plant harboring pSSA-K vector.

Figure 15:
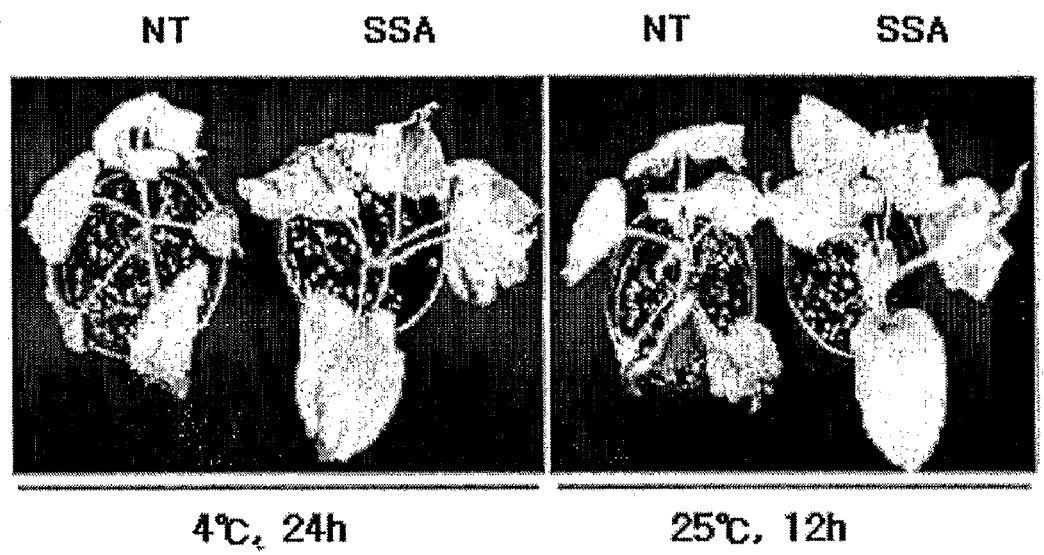
FIG. 15 is a set of photographs and a graph showing the result of the investigation on low temperature resistance of a sweetpotato plant. Precisely, visual plant damage after 24 hour-treatment at 4° C. (A), a photograph of plants which were recovered for 12 hours at 25° C. after the treatment (B), and photosynthetic efficiency during the 24 hour-low temperature treatment at 4° C. and after 12 hour-recovery at 25° C. (C) are shown.
Figure 15:
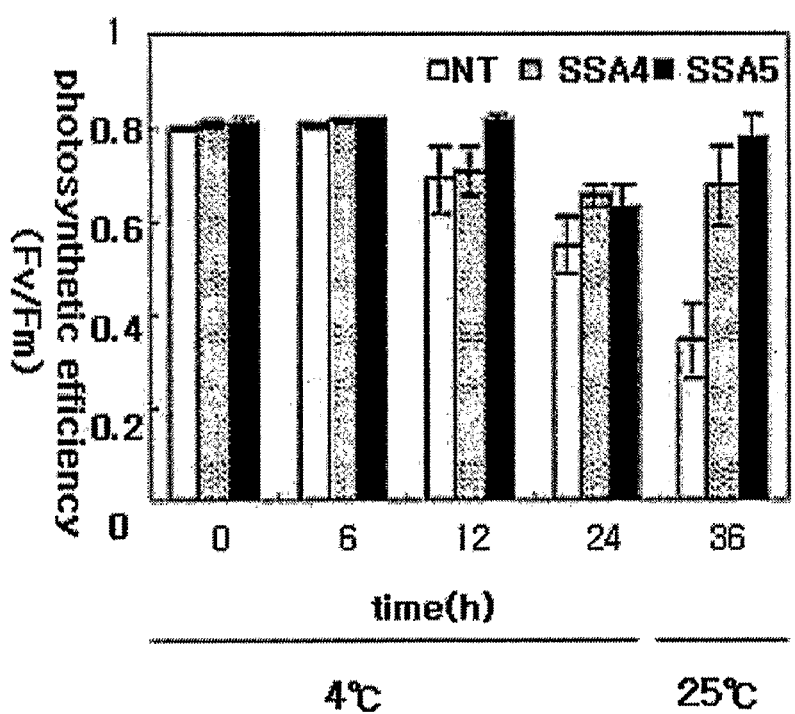

<5-2-3> Resistance Against Stress Caused by Low Temperature of a Sweetpotato Plant In order to investigate resistance against stress caused by low temperature of a transgenic sweetpotato (Variety: Yulmi), NT plant and SSA plant grown for 4 weeks in a greenhouse were exposed on the temperature of 4° C. for 24 hours. As a result, NT plant was wilted, but SSA plant was maintained as normal (FIG. 15A). After low-temperature treatment for 24 hours, plants were recovered at 25° C. for 12 hours. As a result, while NT plant was hardly recovered with still being wilted, SSA plant was almost recovered to the beginning state (FIG. 15B). Photosynthetic efficiencies of NT plant and SSA plant were both 0.8 before the low-temperature treatment. 6 hours after low-temperature treatment, photosynthetic efficiencies of them were not much different from those obtained before the treatment, but photosynthetic efficiency decreased time-dependently from then on. Thus, 24 hours later, photosynthetic efficiency was decreased over 30% in NT plant and so was over 20% in SSA plant. Plants were recovered at 25° C. for 12 hours after low-temperature treatment for 24 hours, and then photosynthetic efficiency was investigated again. As a result, photosynthetic efficiency was still reduced to 60% in NT plant after recovering. In the meantime, photosynthetic efficiency of SSA plant was recovered to the level of before the treatment, even though there was slight difference between individuals (FIG. 15C). In FIGS. 15A-15C, NT: non-transformed sweetpotato plant, SSA4 and SSA5: plants harboring pSSA-K vector.

<5-3> Sulfur Dioxide Resistance

Figure 16:
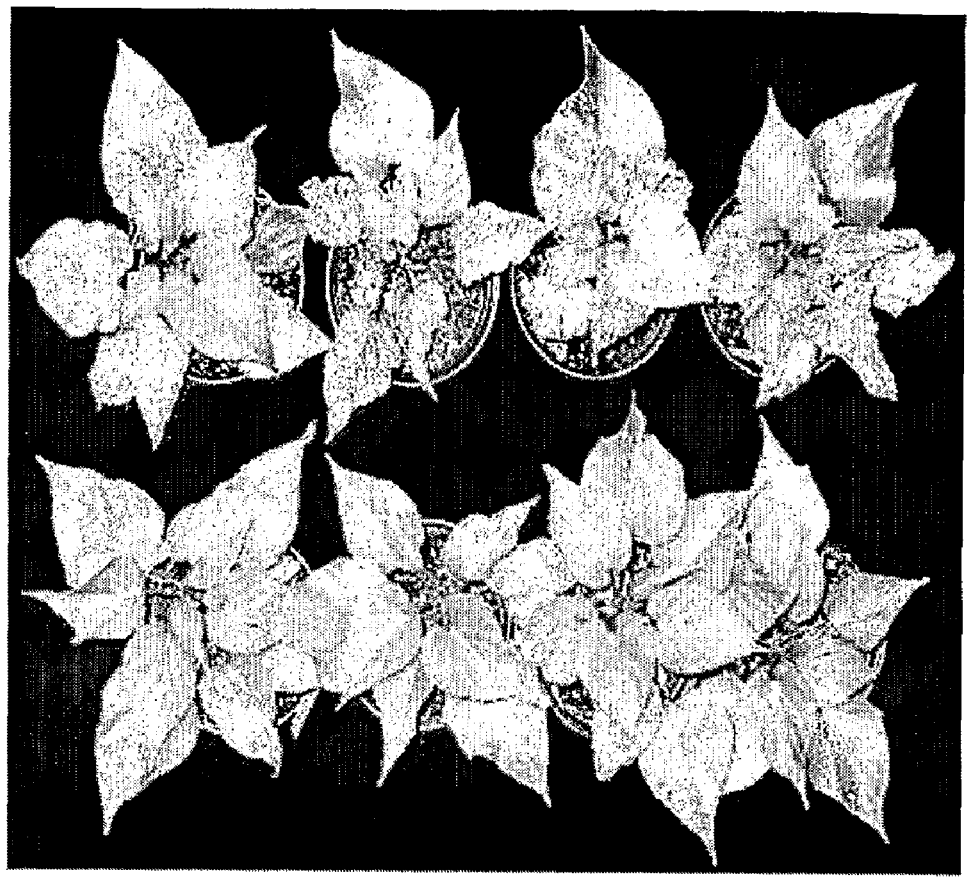
FIG. 16 is a photograph showing the sulfur dioxide resistance of SSA sweetpotato plant resulted from the treatment with 500 ppb of sulfur dioxide for 8 hours a day for 5 days.

In order to investigate sulfur dioxide ($SO_2$) resistance of SSA transgenic sweetpotato plant, NT plant and SSA plant of sweetpotato (Variety: Yulmi) grown for 4 weeks in a green house were treated with 500 ppb of sulfur dioxide, 8 hours a day, for 5 days. As a result, leaves of NT plant were wilted by sulfur dioxide and the growth of the plant was also retarded, comparing to a SSA plant. In the meantime, SSA plant stayed normal and healthy, showing vigorous growth (FIG. 16). In FIG. 16, NT: non-transformant and SSA: sweetpotato plant harboring pSSA-K vector.

Figure 17:
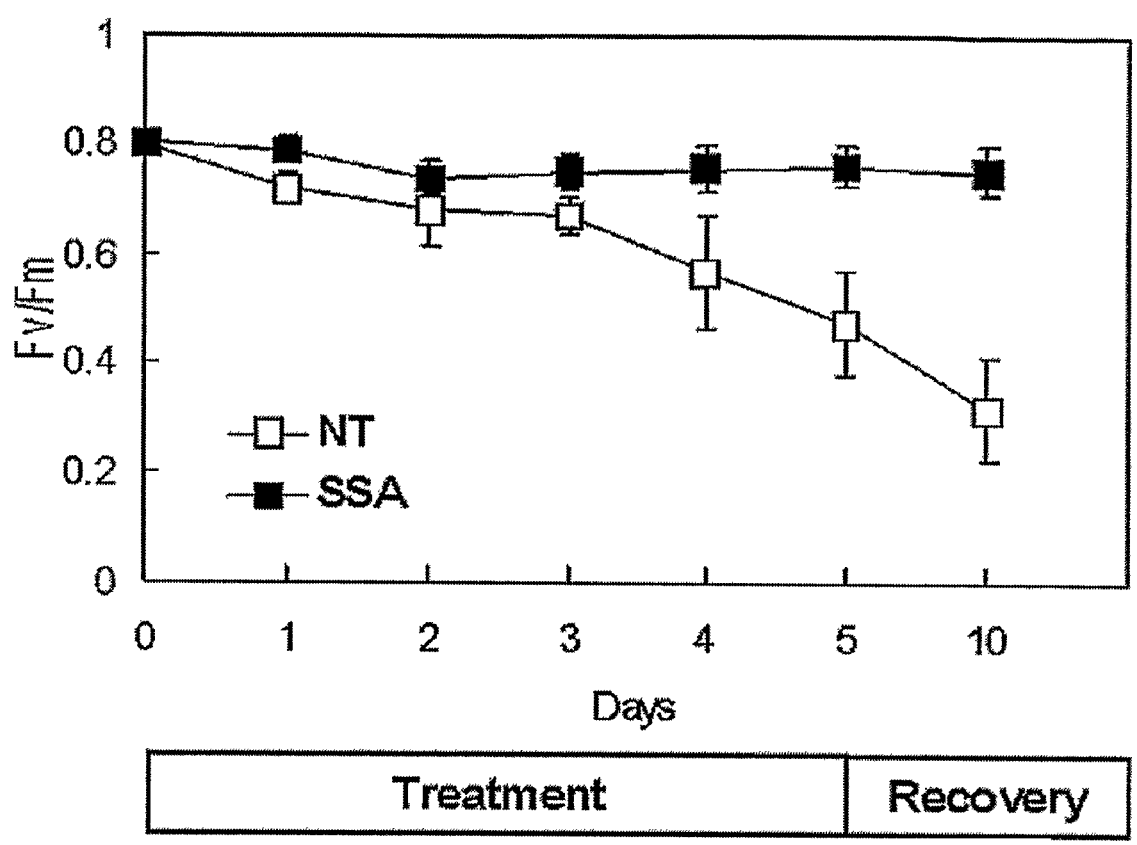
FIG. 17 is a graph showing the photosynthetic efficiency of NT and SSA sweetpotato plants which were obtained during the treatment with 500 ppb of sulfur dioxide for 5 days and after the adaptation to normal condition (0 ppb) for 5 days after the treatment with sulfur dioxide.

Sulfur dioxide resistance of SSA plant was investigated by measuring photosynthetic efficiency. Photosynthetic efficiency in the third leaf from the top of a plant was measured from the next day of sulfur dioxide treatment. As a result, photosynthetic efficiency of SSA plant was gradually decreased from 0.80 (before treatment) to 0.47 on the fifth day. On the contrary, photosynthetic efficiency in SSA plant was hardly decreased after the fifth day from the treatment (still 0.76), suggesting that SSA plant was maintained as healthy, comparing to NT plant (FIG. 17). After the plants were treated with sulfur dioxide, they were grown in a greenhouse for 5 days, during which photosynthetic efficiency was measured. As a result, photosynthetic efficiency of NT plant was 0.32, suggesting that it almost lost photosynthetic function. In the meantime, photosynthetic efficiency in SSA plant was 0.75, indicating that it was almost recovered from damage by sulfur dioxide. In conclusion, SSA plant showed increased resistance against sulfur dioxide, one of the most representative pollutants.

INDUSTRIAL APPLICABILITY

As explained hereinbefore, a transgenic plant transformed with a recombinant expression vector of the present invention for the production of a multiple stress resistant plant shows a strong resistance against oxidative stress inducible herbicides, cold injury, high temperature, salt damage, or various environmental stresses generating oxygen free radicals. Therefore, the vector of the present invention can be a great contribution to the increase of productivity of agricultural crops or mass-production of useful components.

[Sequence List Text]

The SEQ. ID. No 1 and No 2 are primer sequences used for the PCR of SWPA2 promoter performed in Example 1.

The SEQ. ID. No 3 and No 4 are primer sequences used for the PCR of mSOD1 performed in Example 1.

The SEQ. ID. No 5 and No 6 are primer sequences used for the PCR of SWPA2-1 performed in Example 2-2.

The SEQ. ID. No 7 and No 8 are primer sequences used for the PCR of SWPA2-2 performed in Example 3-2.

The SEQ. ID. No 9 and No 10 are primer sequences used for the PCR of APX performed in Example 3-2.

The SEQ. ID. No 11 is a forward primer sequence used for the PCR of mSOD1 performed in Example 4-2.

The SEQ. ID. No 12 is a reverse primer sequence used for the PCR of CaMV 35S terminator performed in Example 4-2.

The SEQ. ID. No 13 and No 14 are primer sequences used for the Southern blot of APX performed in Example 4-2.

The SEQ. ID. No 15 is a nucleotide sequence of oxidative stress inducible SWPA2 promoter originated from *Ipomoea batatas*.

The SEQ. ID. No 16 is a cDNA sequence coding CuZn-SOD of *Manihot seculenta*.

The SEQ. ID. No 17 is a cDNA sequence coding APX of *Pisum sativum*.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

---

The invention claimed is:

1. A recombinant expression vector for the production of multiple stress tolerant plants containing
   oxidative stress inducible peroxidase promoter that is a nucleotide sequence of sweetpotato peroxidase anionic 2 (SWPA2) represented by SEQ ID NO:15,
   the nucleotide sequence of SEQ IDS NO:16 encoding superoxide dismutase (SOD) and the nucleotide sequence of SEQ IDS NO:17 encoding ascorbate peroxidase (APX) operably linked to said promoter,
   antibiotics resistant gene,
   tobacco etch virus (TEV) leader sequence,
   a polynucleotide encoding a transit peptide sequence for chloroplast targeted expression,
   CaMV 35S transcription terminator, and
   T-DNA boarder sequence,
   wherein,
   the recombinant expression vector is pSSA-K, deposited as Accession No: KCTC 10536BP, or pSSA-H, deposited as Accession No: KCTC 10537BP.

2. A transgenic plant transformed with the expression vector of claim 1.

3. The transgenic plant as set forth in claim 2, wherein the plant is selected from a group consisting of potato, sweetpotato and tall fescue.

4. A method for preparing multiple stress tolerant transgenic plants comprising the following steps:
   i) preparing the expression vector of claim 1 for plant transformation comprising SWPA2 promoter, SOD gene and APX gene;
   ii) preparing a transformant by inserting the expression vector prepared in step i) into a plant or culture cells;
   iii) culturing the transformant prepared in step ii); and
   iv) preparing a transgenic plant by regeneration after tissue-culturing the transformant prepared in step iii).

5. The method as set forth in claim 4, wherein the plant or culture cells are selected from the group consisting of potato, sweetpotato and tall fescue.

6. The preparation method as set forth in claim 4, wherein the transformant of step ii) is prepared by particle bombardment.

7. The preparation method as set forth in claim 4, wherein the step ii) is composed of the following sub steps:
   i) introducing the expression vector into *Agrobacteria*; and
   ii) preparing a transformant by co-culturing the *Agrobacteria* with callus or culture cells.

* * * * *

SEQUENCE LISTING

```
<160> NUMBER OF SEQ ID NOS: 17

<210> SEQ ID NO 1
<211> LENGTH: 26
<212> TYPE: DNA
<213> ORGANISM: Artificial Sequence
<220> FEATURE:
<223> OTHER INFORMATION: forward primer of SWPA2 promoter

<400> SEQUENCE: 1
ttaaagcttc catgatcaga tcgata                                        26

<210> SEQ ID NO 2
<211> LENGTH: 24
<212> TYPE: DNA
<213> ORGANISM: Artificial Sequence
<220> FEATURE:
<223> OTHER INFORMATION: backward primer of SWPA2 promoter

<400> SEQUENCE: 2
cgggtctaga ggtcaaagga aaat                                          24

<210> SEQ ID NO 3
<211> LENGTH: 18
```

```
<212> TYPE: DNA
<213> ORGANISM: Artificial Sequence
<220> FEATURE:
<223> OTHER INFORMATION: forward primer of mSOD1 gene

<400> SEQUENCE: 3
gtcgacgtga aggctgaa                                                 18

<210> SEQ ID NO 4
<211> LENGTH: 20
<212> TYPE: DNA
<213> ORGANISM: Artificial Sequence
<220> FEATURE:
<223> OTHER INFORMATION: backward primer of mSOD1

<400> SEQUENCE: 4
gagctctatc ctcgcaaacc                                               20

<210> SEQ ID NO 5
<211> LENGTH: 22
<212> TYPE: DNA
<213> ORGANISM: Artificial Sequence
<220> FEATURE:
<223> OTHER INFORMATION: forward primer of specific SWPA2-1

<400> SEQUENCE: 5
atttatcggc aaggaggagg ta                                            22

<210> SEQ ID NO 6
<211> LENGTH: 19
<212> TYPE: DNA
<213> ORGANISM: Artificial Sequence
<220> FEATURE:
<223> OTHER INFORMATION: backward primer of specific SWPA2-1

<400> SEQUENCE: 6
cccggtgagg tgatttgaa                                                19

<210> SEQ ID NO 7
<211> LENGTH: 24
<212> TYPE: DNA
<213> ORGANISM: Artificial Sequence
<220> FEATURE:
<223> OTHER INFORMATION: forward primer of specific SWPA2-2

<400> SEQUENCE: 7
caccaagtac ccaaaccctc tatt                                          24

<210> SEQ ID NO 8
<211> LENGTH: 23
<212> TYPE: DNA
<213> ORGANISM: Artificial Sequence
<220> FEATURE:
<223> OTHER INFORMATION: backward primer of specific SWPA2-2

<400> SEQUENCE: 8
gttggcgtga ccgtacatta ttg                                           23

<210> SEQ ID NO 9
<211> LENGTH: 21
<212> TYPE: DNA
<213> ORGANISM: Artificial Sequence
<220> FEATURE:
<223> OTHER INFORMATION: forward primer of specific APX

<400> SEQUENCE: 9
```

```
ttcggaacaa ttaagcacca a                                              21

<210> SEQ ID NO 10
<211> LENGTH: 24
<212> TYPE: DNA
<213> ORGANISM: Artificial Sequence
<220> FEATURE:
<223> OTHER INFORMATION: backward primer of specific APX

<400> SEQUENCE: 10
aagagggcgg aatacagagt cagt                                           24

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
gctgaagctg ttcttaccag                                                20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
ctcaacacat gagctaaacc                                                20

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
agaggaagct cagaggtttt                                                20

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
ccaccagata gagcaacaat                                                20

<210> SEQ ID NO 15
<211> LENGTH: 1325
<212> TYPE: DNA
<213> ORGANISM: Ipomoea batatas

<400> SEQUENCE: 15
aagcttccat gatcagatcg ataataccaa atggtaccac ctaactaggt gatatatatt     60
atgtatgtca ttattttaaa ctgtattaca aagactattt tttcattaat tggtacaaag    120
aaaaattaaa cagaaaagaa aggaaaaaat gactcaccac ctagcaccta gacacctaga    180
caccaagtac ccaaaccctc tatttttcaac atctattttc agatgtaaat atgagttgga    240
cgaagaaggt gttagcaatt atttgattaa tcttgctacg ataattatga tccactcact    300
```

-continued

| | | |
|---|---|---|
| tagtcatttt tttcagacca agacaactag cttgagtttt ttattgtatg tggtcggaac | 360 |
| gttttttgta attaaaaaaa taaaagttgc atcattatat atggtagatt aagtaattga | 420 |
| tcaatcaacg tttaattttg catttatcgg caaggtggag gttccaactt ccagtcgaac | 480 |
| ttagagagtc attggagacc ttgaccagtt aactagcggt gtcgaaaacc tgcacaactt | 540 |
| gagatttaat tgcatacctt tatatatga cgcgttttat tttttttttcc tagaaaataa | 600 |
| tttggaagaa ataagaata tgtattctgt gaaagctagg ccaaaacgaa tgtcttttcg | 660 |
| tcgtttcgt taaggttta gatcatattt catctggtcc aacactcaaa cttgtataat | 720 |
| ggacgaatta ttagtcattt tagacctacc ggctagcgcg acttttttgt tttccataaa | 780 |
| gattcgataa ttgcatggcc agatgcaaag tttgaaattt aatgtttgcc aaatcctatc | 840 |
| atacaccaca acacatgtct cagggccaag tggcaccagc aaacattcct gtcataatta | 900 |
| attttttaa tgagaaggag gaaactcaca gctattactc gaaggtatat aatattgagt | 960 |
| aaatcttact ttgtgattct agttgacaaa acaccgcaag ataaactata ctaagttcaa | 1020 |
| atcacctcac cgggttggct cagattggtt ttttcaatac aagagggggt gtgaactccc | 1080 |
| gtgccgacct cttttgaggg acaataatgt acggtcacgc caacctagct tgattttttc | 1140 |
| tgacaaatat attactacat atattacacg gtcaaataat taatcaaaaa ataaaaaaag | 1200 |
| accccaatta aagtccccaa ccactctcaa atattctatt taagggaaac cttagaggca | 1260 |
| attcatgcat cctcaacccc ttcttcttca ttttcttaat cttacatttt cctttgaccc | 1320 |
| tcgag | 1325 |

<210> SEQ ID NO 16
<211> LENGTH: 801
<212> TYPE: DNA
<213> ORGANISM: Manihot esculenta

<400> SEQUENCE: 16

| | | |
|---|---|---|
| tctcgatctt ctctgtctaa gctctaaagg ggtgctctga gatcacgtaa aacaatggtg | 60 |
| aaggctgaag ctgttcttac cagtagtgag ggggttagcg gaacaatctt ctttacccaa | 120 |
| gaaggagatg gtcctaccac tgtaactgga acatttccg gccttaagcc agggcttcat | 180 |
| gggttccacg tccatgccct tggagacaca acaaacggtt gcatgtcaac tgggccacac | 240 |
| tttaaccctt ctggcaaaga tcatggtgcc cctgaggatg agattcgtca tgctggtgat | 300 |
| ctgggaaatg tcactgctgg tgatgatggc actgctagtt tcacaattat tgacaagcat | 360 |
| attcctcttt ctggtcaaaa ttcaatcata ggaagggcag ttgttgttca tgcagatcct | 420 |
| gatgatcttg gcaggggagg acatgaactc agtaaaacca ccggaaatgc tggtggcaga | 480 |
| gtagcatgcg gtattattgg tttgcgagga tagagtgctt ctccagagat caataacaag | 540 |
| acaaagacag ctgaaacatg cacagccgga caacctttag aagaacgtta ggagaccatt | 600 |
| aactcatttg aataaaagaa agaataatac tgtagttttg gctggtttgg tcttgtgatc | 660 |
| tcaagatggt gtatgctttg tatggttccg tgaagtttat tgaactttga acttttttcga | 720 |
| atggtagggc ttgctctttg tctggtccaa attcaggccg tggatgttttt atactgcttt | 780 |
| aaaaaaaaaa aaaaaaaaaa a | 801 |

<210> SEQ ID NO 17
<211> LENGTH: 1054
<212> TYPE: DNA
<213> ORGANISM: Pisum sativum

```
<400> SEQUENCE: 17
gaattcggct tgtgctctcc tcgtgtcact agggtttaac ttcttcgttt ttgcttctta        60
gatttcgaga atcgtttgct atgggaaaat cttacccaac tgttagtccc gattaccaga       120
aggccattga aaaggctaag aggaagctca gaggttttat cgctgagaag aaatgcgctc       180
ctctaattct ccgtttggca tggcactctg ctggtacttt tgattccaag acaaagactg       240
gtggtccttt cggaacaatt aagcaccaag ctgagcttgc tcatggtgct aacaacggtc       300
ttgatatcgc ggttaggctg ttggagccta ttaaggagca attccctatt gtgagctatg       360
ctgatttcta ccagttggct ggtgttgttg ctgttgagat taccggtgga cctgaagttc       420
ctttccaccc tggtagggag gacaagcctg agccaccacc tgagggtcgc ttgcctgatg       480
ccactaaggg ttctgaccat ttgagggatg tgtttggaaa ggctatgggg cttagtgatc       540
aggacattgt tgctctatct ggtggtcaca ccattggagc tgcacacaag gagcgttctg       600
gatttgaggg accatggact tctaatcctc tcattttga caactcatat ttcactgagt       660
tgttgactgg tgagaaggat ggccttcttc agttgccaag tgataaggca cttttgactg       720
actctgtatt ccgccctctt gttgagaaat atgctgcgga tgaagatgtt ttctttgctg       780
attatgctga agcacatctt aagctctctg agcttggatt tgctgaagcc taagtcacag       840
ttgtttggtg tttagagagg agcactgtcc tgaatcttac ataaatttca tagacgttgc       900 ttttatttc aatgtgattc atcttagttg ggtagcattt tggatgtatt ttggaagttt       960
gattgttttc tctattgttg atccttggtt aaataacatt gttaagtggt aatgcccagc      1020
tattgcattt tcctgataaa aaaaaaaccg aatt                                  1054
```